United States Patent
Yamagata et al.

(10) Patent No.: US 11,612,361 B2
(45) Date of Patent: Mar. 28, 2023

(54) INFORMATION DISPLAY SYSTEM, INFORMATION DISPLAY DEVICE, AND COMPUTER-READABLE RECORDING MEDIUM

(71) Applicants: Hideaki Yamagata, Kanagawa (JP); Noriyuki Tomita, Ishikawa (JP); Aritaka Hagiwara, Ishikawa (JP); Shinya Mukasa, Shizuoka (JP); Yutaka Yagiura, Kanagawa (JP); Daisuke Sakai, Tokyo (JP)

(72) Inventors: Hideaki Yamagata, Kanagawa (JP); Noriyuki Tomita, Ishikawa (JP); Aritaka Hagiwara, Ishikawa (JP); Shinya Mukasa, Shizuoka (JP); Yutaka Yagiura, Kanagawa (JP); Daisuke Sakai, Tokyo (JP)

(73) Assignee: RICOH COMPANY, LTD., Tokyo (JP)

( * ) Notice: Subject to any disclaimer, the term of this patent is extended or adjusted under 35 U.S.C. 154(b) by 551 days.

(21) Appl. No.: 16/297,884

(22) Filed: Mar. 11, 2019

(65) Prior Publication Data
US 2019/0282181 A1 Sep. 19, 2019

(30) Foreign Application Priority Data

Mar. 15, 2018 (JP) .............................. JP2018-047427
Sep. 18, 2018 (JP) .............................. JP2018-174308

(51) Int. Cl.
*A61B 5/00* (2006.01)
*G06F 3/0482* (2013.01)

(52) U.S. Cl.
CPC .......... *A61B 5/7282* (2013.01); *A61B 5/0033* (2013.01); *A61B 5/7435* (2013.01); *G06F 3/0482* (2013.01)

(58) Field of Classification Search
CPC ... A61B 5/7282; A61B 5/7235; A61B 5/7435; A61B 5/316; A61B 5/0033; A61B 5/245; A61B 5/369; A61B 5/721
See application file for complete search history.

(56) References Cited

U.S. PATENT DOCUMENTS

2005/0283068 A1* 12/2005 Zuccolotto ............. A61B 5/055
600/410
2011/0219325 A1* 9/2011 Himes .................... G16H 40/63
715/771

(Continued)

FOREIGN PATENT DOCUMENTS

| JP | 2000-102516 | 4/2000 |
| JP | 2005-095469 | 4/2005 |

(Continued)

OTHER PUBLICATIONS

Thomas R. Knösche, "Transformation of Whole-Head MEG Recordings Between Different Sensor Positions", Biomedizinische Technik, 2002, vol. 47 No. 3, p. 59-62.

(Continued)

*Primary Examiner* — Mallika D Fairchild
(74) *Attorney, Agent, or Firm* — Harness, Dickey & Pierce, P.L.C.

(57) ABSTRACT

According to an embodiment, an information display system includes a displacement measurement unit, a display unit, and a controller. The displacement measurement unit measures displacement of a measurement part. The display unit displays a time axis of signal detection. The controller controls the displacement measurement unit and the display unit. When a signal that is output from the displacement measurement unit meets a given condition, the controller determines that displacement of the measurement part is detected and displays detection information representing (Continued)

that the displacement is detected in any one of a time position and a time area on the display unit in which the displacement is detected.

20 Claims, 18 Drawing Sheets

(56) References Cited

U.S. PATENT DOCUMENTS

| | | | | |
|---|---|---|---|---|
| 2011/0249088 | A1* | 10/2011 | Hannibal | A61B 5/066 348/43 |
| 2012/0136273 | A1* | 5/2012 | Michelson, Jr. | A61B 5/291 600/544 |
| 2013/0231578 | A1 | 9/2013 | Takayanagi et al. | |
| 2013/0245463 | A1 | 9/2013 | Stuebe et al. | |
| 2015/0196780 | A1* | 7/2015 | Tijs | A61N 5/1049 600/1 |
| 2016/0029958 | A1* | 2/2016 | Le | A61B 5/6803 600/383 |
| 2017/0231519 | A1* | 8/2017 | Westover | A61B 5/291 600/544 |
| 2018/0071530 | A1* | 3/2018 | Giftakis | A61N 1/36142 |
| 2018/0268588 | A1 | 9/2018 | Shinohara et al. | |
| 2018/0317848 | A1* | 11/2018 | Gunasekar | A61B 5/7246 |

FOREIGN PATENT DOCUMENTS

| | | |
|---|---|---|
| JP | 4229489 | 2/2009 |
| JP | 2011-083433 | 4/2011 |
| JP | 2012-055514 | 3/2012 |
| JP | 2013-059621 | 4/2013 |
| JP | 2013-158415 A | 8/2013 |
| JP | 2013-208420 | 10/2013 |
| JP | 2018-089336 | 6/2018 |

OTHER PUBLICATIONS

Kazuyuki Kose, et al., "Head position correction in magnetoencephalography with optical tracking device", The journal of Japan Biomagnetism and Bioelectromgnetics Society, 2010, vol. 23, No. 1, p. 186-187.
JP Office Action for corresponding Japanese Patent Application No. 2018-174308 dated Aug. 9, 2022.

* cited by examiner

FIG.7

| | | Annotation List | | | ▼ |
|---|---|---|---|---|---|
| ☑ Show Markup on wave — 180a | | | | | |
| No. | File | Time | Event | MEMO | Cluster |
| 2 ☐ | 001 | 00:09:30 | 🔥 | normal spike | B |
| 1 ☐ | 001 | 00:05:00 | 🔥 | strong spike | A |
| 0 ☐ | 000 | 00:00:00 | 🔥 | Dr.memo | A |
| 3 ☐ | 001 | 00:10:00 | ⚘ | body motion | B |

180

Exit Measurement

FIG.13

INFORMATION DISPLAY SYSTEM, INFORMATION DISPLAY DEVICE, AND COMPUTER-READABLE RECORDING MEDIUM

CROSS-REFERENCE TO RELATED APPLICATIONS

The present application claims priority under 35 U.S.C. § 119 to Japanese Patent Application No. 2018-47427, filed on Mar. 15, 2018 and Japanese Patent Application No. 2018-174308 filed in Japan on Sep. 18, 2018. The contents of which are incorporated herein by reference in their entirety.

BACKGROUND OF THE INVENTION

Field of the Invention

The present invention relates to an information display system, an information display device, and a computer-readable recording medium.

Description of the Related Art

A method of adding a comment to a biological signal of a patient, which is a biological signal being monitored, at any timing, registering the biological signal with the comment, and displaying data on the registered biological signal at any timing is known (for example, see Japanese Unexamined Patent Application Publication No. 2005-95469). In this known technology, a requested area of a single waveform being monitored is specified and the specified area is saved with a comment and, when a display is made, the comment is displayed together with the single waveform. The comment is displayed in a free space on a waveform display screen.

Furthermore, it is known that, in a technology to display waveforms and digital annotations in a chart area in which physiological information is displayed, multiple types of physiological signal (for example, a fetus heart rate signal and an intrauterine pressure signal) can be plotted in synchronization with each other along the same time axis (for example, see Japanese Unexamined Patent Application Publication No. 2013-59621).

The known technology using digital annotations does not disclose a specific method about how digital annotations are input to multiple types of biological signal and how the digital annotations are displayed. Each of the multiple types of biological signal is represented by a single waveform.

In recent years, there has been a progress in studying brain neural activities and development of magnetoencephalographs and electroencephalographs have been progressing. In a magnetoencephalograph or an electroencephalograph, faint signal waveforms from a large number of sensors are collected to obtain one type of biological signal. When such a faint brain signal is measured and if a measurement part at which the measurement is performed (for example, the head for brain) moves, a correct signal cannot be measured. Analyzing the result of measurement without noticing the move of the measurement part leads to a problem in that correct analysis is not performed.

In order to solve the problem, some methods to hold the measurement part with a tool have been proposed (see Japanese Unexamined Patent Application Publication No. 2011-83433, Japanese Unexamined Patent Application Publication No. 2012-55514, and Japanese Unexamined Patent Application Publication No. 2000-102516). These methods have certain effectiveness to subject's unintentional move of a measurement part; however, it is difficult to deal with subject's intentional move of a measurement part, for example, when measurement is performed on a child. It is extremely difficult to hold a measurement part of a child securely enough to prevent child's intentional move. Even if the measurement part is held, brain activities are thus caused and it is extremely highly likely that originally intended measurement is not performed.

In view of the above-described circumstances, there is a need to provide an information display system, an information display device, and a computer readable recording medium having a program that enable, even when there is displacement of a measurement part, prevention of incorrect analysis and analysis in a short time.

SUMMARY OF THE INVENTION

According to an embodiment, an information display system includes a displacement measurement unit, a display unit, and a controller. The displacement measurement unit measures displacement of a measurement part. The display unit displays a time axis of signal detection. The controller controls the displacement measurement unit and the display unit. When a signal that is output from the displacement measurement unit meets a given condition, the controller determines that displacement of the measurement part is detected and displays detection information representing that the displacement is detected in any one of a time position and a time area on the display unit in which the displacement is detected.

BRIEF DESCRIPTION OF THE DRAWINGS

FIG. 7 is a diagram of an annotation list;

FIG. 13 is a diagram of a screen displayed right after a specific annotation line is chosen on the analysis screen in FIG. 11;

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
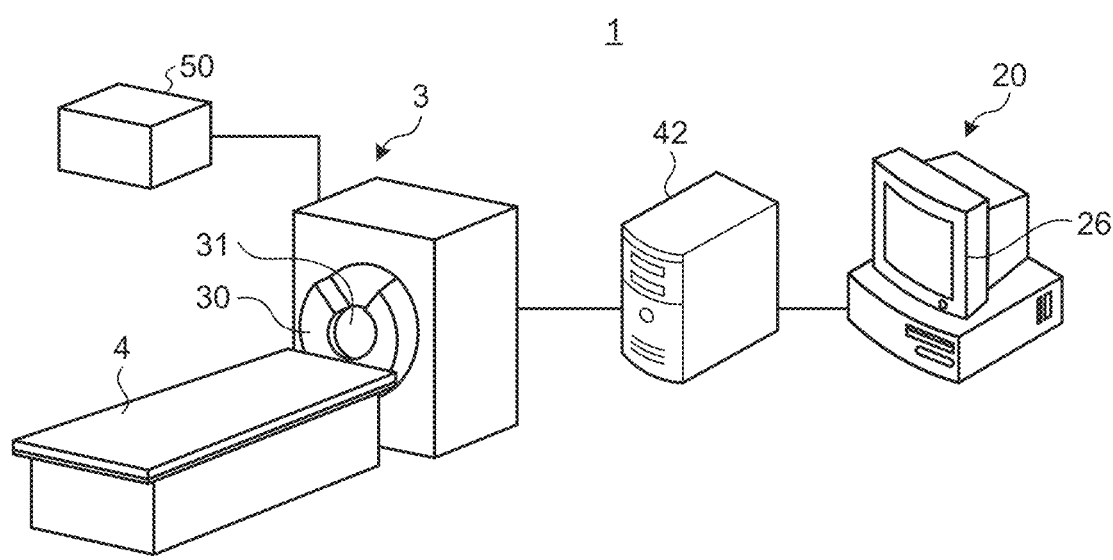
FIG. 1 is an external view of a biological signal measurement system according to an embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of an information display system, an information display device, and a computer-readable recording medium will be described in detail bellow with reference to the accompanying drawings.

FIG. 1 is an external view of a biological signal measurement system 1 serving as an exemplary application of an information display technology according to the embodiment. The biological signal measurement system 1 measures and displays multiple types of biological signal, such as MEG (magneto-encephalography) signal and EEG (electro-encephalography) signal. The biological signal measurement system 1 includes a measurement device 3, a data recording server 42, an information display system 20, and a head position measurement device 50 that measures the position of the head of a measurement subject on which measurement is performed.

The information display system 20 includes a monitor display (a display device) 26 that displays signal information obtained through measurement and a result of analysis. FIG. 1 illustrates the data recording server 42 and the information display system 20 separately. Alternatively, at least part of the data recording server 42 may be incorporated into the information display system 20. The head position measurement device 50 is a displacement measurement unit that measures displacement of a measurement part on which measurement is performed and that outputs a signal.

The measurement subject lies supine on a measurement table 4 with his/her head having electrodes (or sensors) for EEG measurement attached thereto and puts his/her head in a hollow 31 of a Dewar 30 of the measurement device 3. The Dewar 30 is a container that maintains an ultralow-temperature environment using liquid helium and in which a large number of magnetic sensors for MEG measurement are arranged on the inner side the hollow 31 of the Dewar 30. The measurement device 3 collects EEG signals from the electrodes, MEG signals from the magnetic sensors, and head position information from the head position measurement device 50 and outputs the collected biological signals to the data recording server 42. The data that is recorded in the data recording server 42 is read, displayed and analyzed by the information display system 20. In general, the Dewar 30 incorporating the magnetic sensors and the measurement table 4 are arranged in a magnetic shielding room; however, the magnetic shielding room is omitted for convenience of illustration in FIG. 1.

The information display system 20 displays waveforms of the MEG signals from the magnetic sensors and the waveforms of the EEG signals from the electrodes on the same time axis in synchronization with each other. The EEG signals represent the electric activities of nerve cells (the flow of ion charges occurring at dendrites of neurons in synaptic transmission) as voltage values between electrodes. The MEG signals represent minute variations of magnetic fields generated by the electric activities of the brain. Brain magnetic fields are sensed by a highly sensitive superconducting quantum interference device (SQUID) sensor.

Figure 2:
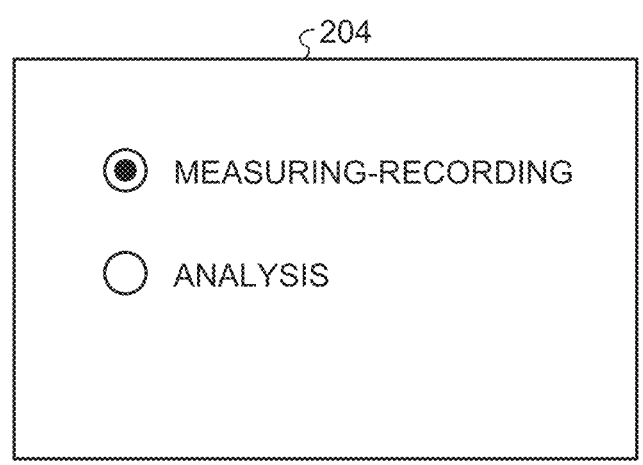
FIG. 2 is a diagram of an exemplary start screen.

FIG. 2 is a diagram of an exemplary start screen 204 that is displayed on the monitor display 26. On the start screen 204, "measuring-recording" and "analysis" choice boxes are displayed. In any one or both of EEG measurement and MEG measurement, measuring and recording data and analyzing the data are often performed by different units, respectively. For example, when the "measuring-recording" box is chosen by a measurement technologist (measurer), the data that is measured by the measurement device 3 is sequentially saved in the data recording server 42, is read by the information display system 20, and is displayed on the monitor display 26. After the measuring and recording end, when a doctor chooses the "analysis" box, the recorded measurement data is read and analyzed. Specific modes of measuring and recording and analysis will be described below.

Operations During Measuring and Recording

Figure 3:
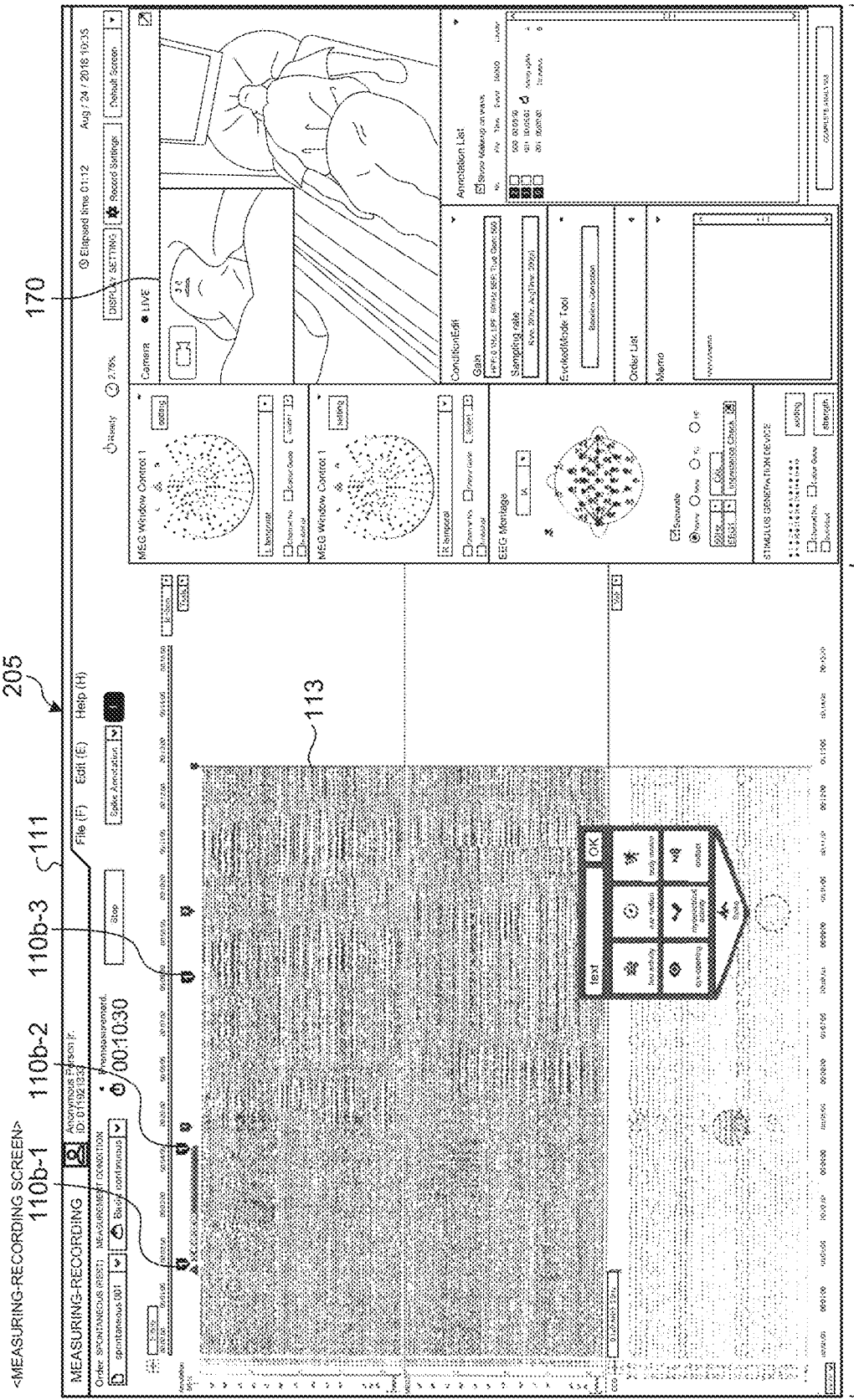
FIG. 3 is a diagram of an exemplary measuring-recording screen.

FIG. 3 is a diagram of an exemplary measuring-recording screen 205. A tab 111 on the screen displays that this is the "measuring-recording" screen. The measuring-recording screen includes an area 201A to display measured signal waveforms and an area 201B to display monitor information other than signal waveforms. The area 201A to display signal waveforms is arranged on the left on the screen when viewed from the measurer and the area 201B to display monitor information other than signal waveforms is arranged on the right on the screen when viewed from the measurer. Any extra shift is caused in the measure's view in accordance with the shift in the waveforms that are detected and displayed in real time (displayed from the left side to the right side on the screen) and in moving the mouse from the area 201A on the left on the screen to the area 201B on the right on the screen, which improves operation efficiency.

On the area 201B on the display screen, a monitor window 170 for checking the condition of the measurement subject during measurement is displayed. Displaying a live video of the measurer during measurement enables enhancement of reliability of checking signal waveforms and determination. FIG. 3 illustrates that the whole measuring-recording screen is displayed on the display screen of the single monitor display 26. Alternatively, the area 201A on the left and the area 201B on the right may be displayed independently on two or more monitor displays separately.

Figure 4:
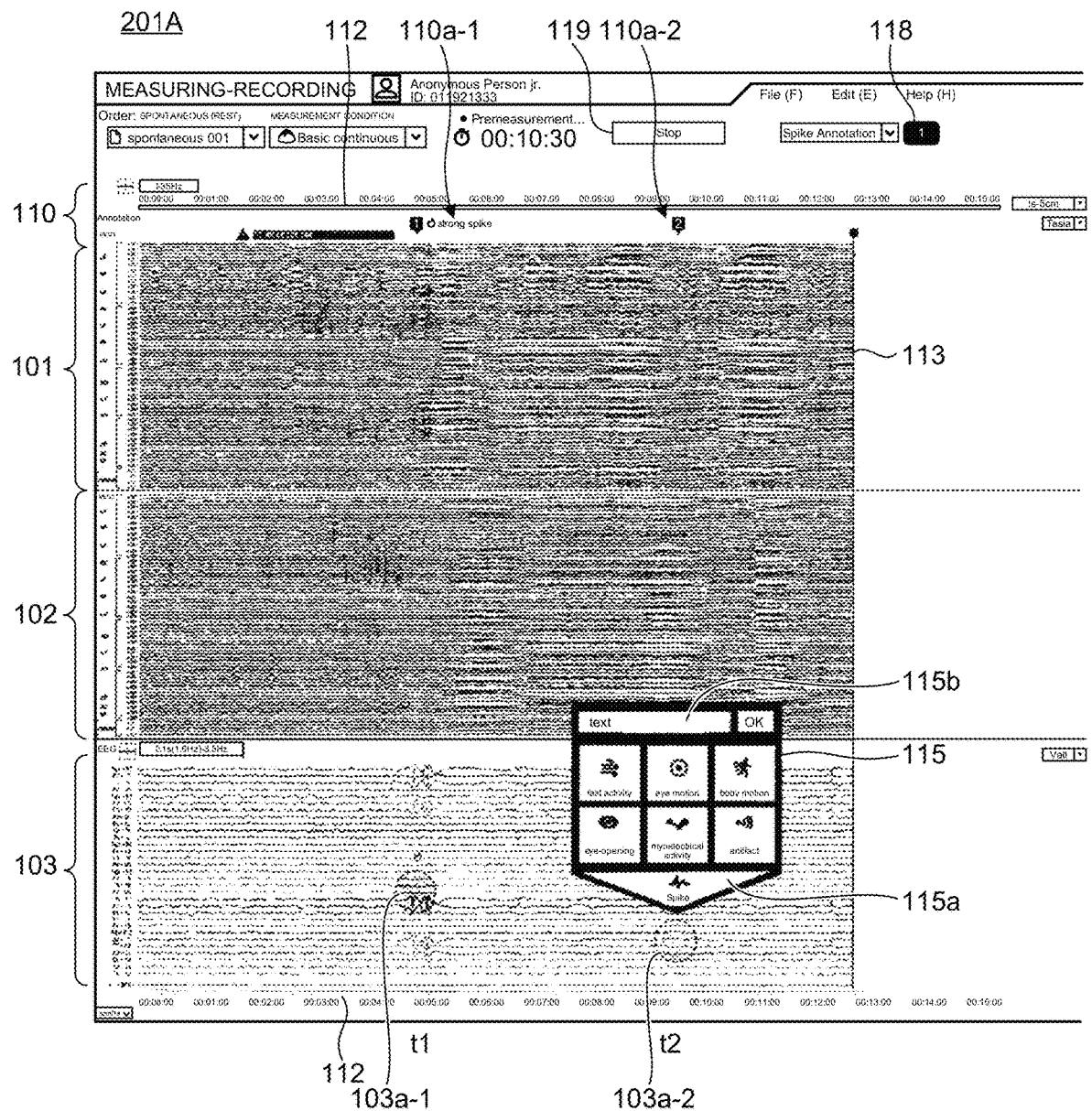
FIG. 4 is an enlarged view of the area on the left in the measuring-recording screen in FIG. 3.

FIG. 4 is an enlarged view of the area 201A on the left in FIG. 3. The area 201A includes a display part 110 serving as a first display part to display signal detection time information in a horizontal direction of the screen (in a first direction) and display parts 101 to 103 serving as a second display part to display a plurality of signal waveforms based on signal detection in parallel in the vertical direction of the screen (in a second direction).

The time information displayed on the display part 110 is, in the example in FIG. 4, a timeline containing time displays added along a time axis 112. Only the band-like axis may be displayed without display of the times (numbers) or only the times (numbers) may be displayed without provision of the axis. Alternatively, in addition to the display part 110 on the upper side of the screen, the time axis 112 may be displayed under the display part 103 to display the timeline.

In the area 201A, a plurality of signal waveforms that are acquired from the sensors of the same type or signal waveforms of multiple types that are acquired from a group of sensors of multiple types are displayed in synchronization with each another along the same time axis. For example, the waveforms of the MEG signals that are obtained from the right side of the head of the measurement subject are displayed in parallel on the display part 101 and the waveforms of the MEG signals that are obtained from the left side of the head of the measurement subject are displayed in parallel on the display part 102. On the display part 103, the waveforms of a plurality of EEG signals are displayed in parallel. The EEG signal waveforms are voltage signals that are each measured between electrodes. Each of the signal waveforms is displayed in association with the identification number of the sensor by which the signal is acquired or in association with a channel number.

When measurement is started and measurement information from each sensor is collected, signal waveforms are displayed from the left end of each of the display parts 101 to 103 of the area 201A to the right over time. A line 113 represents the time (present) and moves from the left to the right on the screen. When the signal waveforms are displayed to the right end of the area 201A (the right end of the time axis), the signal waveforms disappear gradually from the left end of the screen to the right, new signal waveforms are displayed in the position of the disappearance sequentially from the left to the right and the line 113 also moves from the left end to the right. The elapse of time is displayed on the time axis 112 in accordance with the progress of measurement in the horizontal display part 110. The measuring and recording is continued until an end button 119 is pressed.

On noticing waveform unsteadiness or an amplitude singularity on a signal waveform while recording data, the measurer (the recorder) is able to mark a problematic spot or area on the signal waveform. It is possible to specify the spot or area to be marked by a pointer operation or a click operation with a mouse. The specified spot (or area) is displayed in an enhanced manner on the signal waveforms in the display parts 101 to 103 and is displayed along the time axis 112 in the display part 110 in a time position or a time range that the specifying result corresponds. The information on the marking containing the display on the time axis 112 is saved together with the signal waveform data. The specified spot corresponds to a time and the specified area corresponds to a certain area containing the time.

In the example in FIG. 4, an area containing at least one channel in the display part 103 is specified at a time t1 and a time containing the time t1 is displayed in a highlighted manner with a mark 103a-1. An annotation 110a-1 representing the specifying result is displayed in a corresponding time position in the display part 110 in connection with the display of the mark 103a-1. Another waveform position or the vicinity of the waveform position is marked in the display part 103 at a time t2 and a mark 103a-2 is displayed in a highlighted manner in the position (the time t2) or an area near the position (at least any one of a time range and waveforms is specified). At the same time, an annotation 110a-2 is displayed in a corresponding time position (time range) in the display part 110.

The annotation 110a-1 added to the display part 110 at the time t1 contains, for example, an annotation identification number and information representing the attribute of the waveform. In this example, together with an annotation number "1", an icon representing the waveform attribute and text information "strong spike" are displayed.

When the measurer specifies another waveform spot or an area near the spot at the time t2, the mark 103a-2 is displayed in a highlighted manner in the specified spot and an annotation number "2" is displayed in a corresponding time position in the display part 110. A pop-up window 115 for choosing an attribute is displayed in the spot displayed in a highlighted manner. The pop-up window 115 includes choice buttons 115a to choose various attributes and an input box 115b to input a comment or additional information. On the choice buttons 115a, causes of waveform unsteadiness, such as "fast activity", "eye motion", "body motion" and "spike", are represented as the waveform attributes. The measurer is able to check the condition of the measurement subject on the monitor window 170 in the area 201B of the screen and accordingly is able to properly choose the attribute representing the cause of the waveform unsteadiness. For example, when a spike occurs in a waveform, it is possible to determine whether the spike is one representing the symptom of epilepsy or one resulting from a body motion (such as sneezing) of the measurement subject.

The same operation is performed at the time t1 and, according to FIG. 4, the choice button 115a of "spike" is chosen on the pop-up window 115 and "strong spike" is entered in the input box 115b and accordingly the annotation 110a-1 is displayed in the display part 110. Such a display mode makes it possible to, when a large number of signal waveforms are displayed in synchronization with one another on the same time axis 112, easily specify a spot or area of interest in the signal waveforms by checking by sight and easily grasp basic information of the spot of interest.

Part of or all the annotation 110a-1, for example, at least one of the attribute icon and the text annotation may be displayed near the mark 103a-1 on the signal waveforms in the display part 103. Adding annotations onto the signal waveforms may hinder checking the waveform shapes and therefore it is desirable that, when annotations are displayed on the signal waveforms in the display parts 101 to 103, it is possible to choose displaying or not displaying the annotations.

A counter box 118 displays the cumulative total of spike annotations. Every time "spike" is chosen, the counter value of the counter box 118 is incremented and this makes it possible to see the total of spikes from the start of recording until now (the line 113) at one sight.

Figure 5:
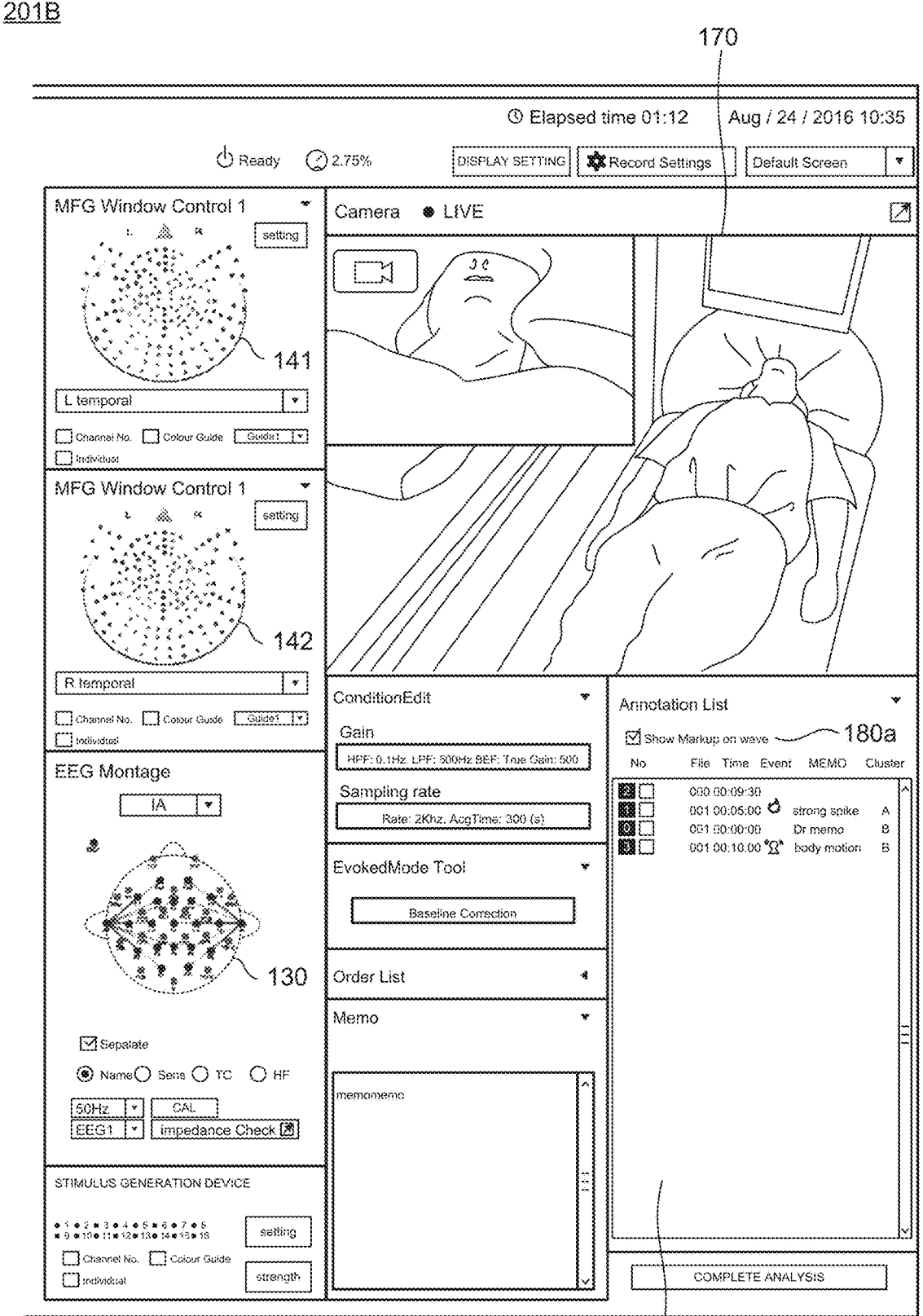
FIG. 5 is an enlarged view of the area on the right in the measuring-recording screen in FIG. 3.

FIG. 5 is an enlarged view of the area 201B on the right on the measuring-recording screen. FIG. 5 illustrates the state at the same time as that according to FIG. 4 (the time point of the line 113). A live video of the condition of the measurement subject lying on the measurement table 4 with the head being in the measurement device 3 is displayed on the monitor window 170 of the area 201B. Distribution maps 141, 142 and 130 that correspond respectively to the sets of signal waveforms in the display parts 101, 102 and 103 and an annotation list 180 are displayed in the area 201B. The annotation list 180 is a list of annotations of the marks on the signal waveforms in FIG. 4. Every time a position or an area on the signal waveforms is specified in the display parts 101 to 103 and an annotation is added, corresponding information is added sequentially to the annotation list 180. The addition to and display of the annotation list 180 on the measuring-recording screen is performed, for example, in the descending order (new data is displayed on the top); however, the order is not limited to this example. The display of the annotation list 180 may be performed in the ascending order, but, note that the correspondence relationship with the annotations displayed along the time axis 112 in the display part 110 is understandable. Furthermore, it is also possible to change the display order or perform sorting according to each item.

In the example in FIG. 5, the time information corresponding to the annotation number "1" and the added annotation information are listed. An attribute icon representing "spike" and texts "strong spike" are recorded as the annotation information. The time information corresponding to the annotation number "2" is listed at the time when the mark 103*a*-1 is displayed in a highlighted manner.

In the example in FIG. 5, the time information corresponding to the annotation number "3" and the added annotation information are listed. An attribute icon representing "body motion" representing that the head has moved and texts "body motion" are recorded as the annotation information.

A displaying/not-displaying choice box 180*a* is arranged near the annotation list 180. When not-displaying is chosen on the choice box 180*a*, the annotations other than the highlighted mark on the signal waveforms are not displayed on the display parts 101 to 103 but the display of the annotations along the time axis 112 in the display part 110 is maintained. This makes the annotation information recognizable without hindering visibility of the signal waveforms.

Figure 6:
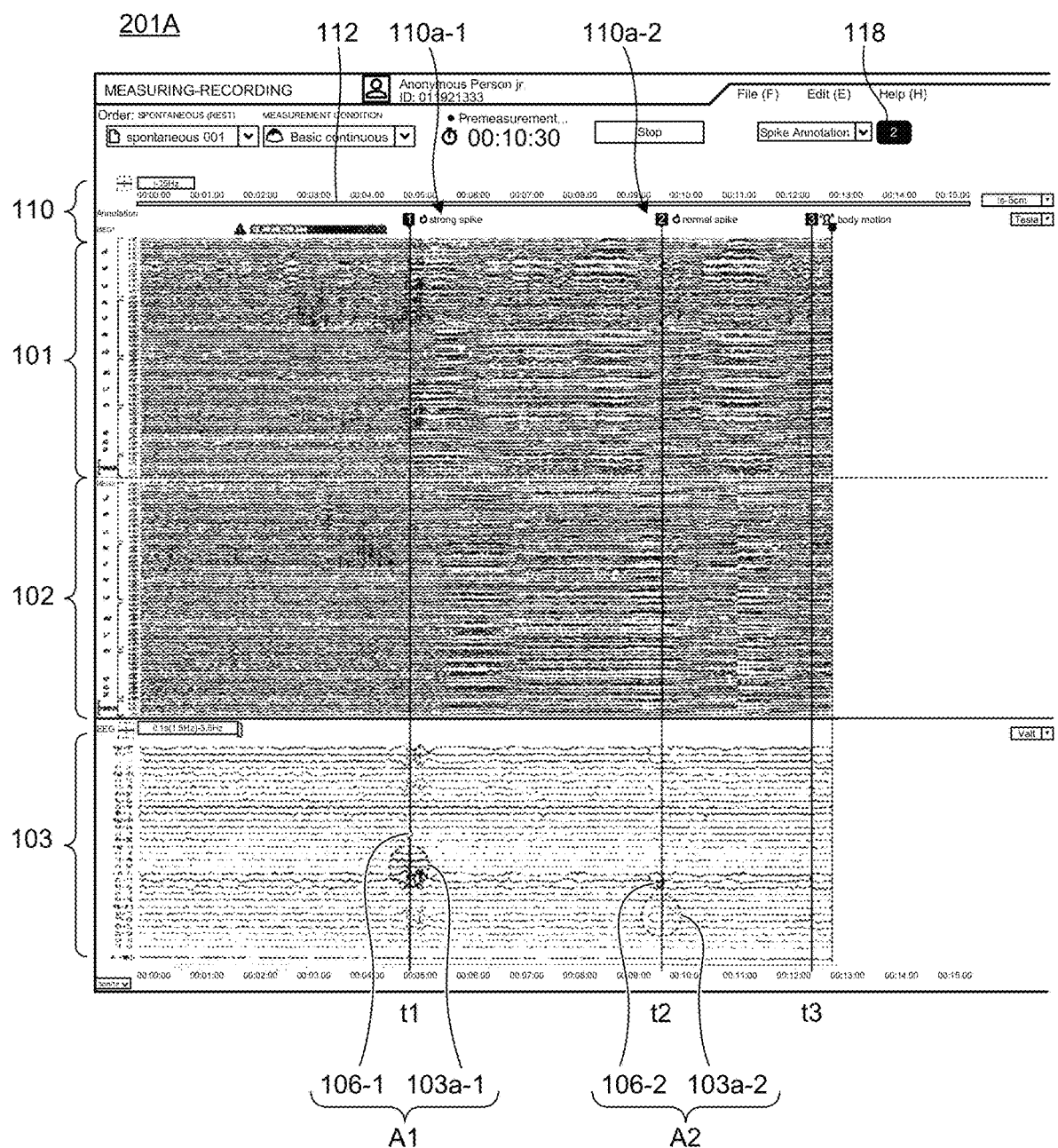
FIG. 6 is a diagram of a screen to which annotation information is input.

FIG. 6 is a diagram of a screen to which annotation information is input. FIG. 6 illustrates a screen in which "spike" on the pop-up window 115 is chosen and texts "normal spike" are input at the time t2 and "body motion" on the pop-up window 115 is chosen and texts "body motion" are input at the time t3. Once the "OK" button is chosen on the pop-up window 115 exemplified in FIG. 4, the pop-up window 115 closes and the annotation 110*a*-2 is displayed in a corresponding time position in the display part 110 as illustrated in FIG. 6. The attribute icon representing "spike" and text information "normal spike" are displayed in association with the annotation number "2". The attribute icon representing "body motion" and text information "body motion" are displayed in association with the annotation number "3". At the same time, the value of the counter box 118 is incremented. An attribute icon 106-2 is displayed near the mark 103*a*-2 displayed in a highlighted manner. In the example, an attribute icon 106-1 is displayed near the mark 103*a*-1 and, as described above, it is possible to choose whether to display or not to display the attribute icons 106-1 and 106-2. An annotation A1 containing the mark 103*a*-1 and the attribute icon 106-1 and an annotation A2 containing the mark 103*a*-2 and the attribute icon 106-2 are contained in the annotation information.

FIG. 7 illustrates the annotation list 180. Addition of the annotation corresponding to the mark 103*a*-2 to the area 201A on the left on the screen updates the annotation list 180. A memo "normal spike" is added to the annotation number "2". A memo "body motion" is added to the annotation number "3".

Thereafter, in the same manner, every time a given spot or area on the signal waveforms is specified in the area 201A during the measuring, the specified spot is displayed in an enhanced manner and annotation information is displayed along the time axis 112 in the display part 110. In the area 201B, annotation information is added sequentially to the annotation list 180.

In the annotation list 180 and the area 201A on which the signal waveforms are displayed, displaying annotation numbers is not essential and need not be used. Any information may be used as identification information as long as the information identifies the added annotation. For example, an attribute icon and an attribute character string (such as "strong spike") may be displayed near the time axis in association with a time. Furthermore, a file number (the number displayed in the item "File" in FIG. 6) may be displayed together in the area 201A.

When the end button 119 (illustrated in FIG. 4) is chosen (pressed) and the measurement ends, the highlighted spots that are specified in the display parts 101 to 103 are saved in association with the signal waveforms. The annotation information that is displayed in the corresponding time positions in the display unit 110 is also saved in association with the annotation numbers and the times. Relative information, such as the counter value of the counter box 118 and the content of the annotation list 180, is also saved. Saving the display information enables, even when the measurer and the analyzer are different from each other, the analyzer to recognize the problematic spot easily and analyze the spot.

Figure 8:
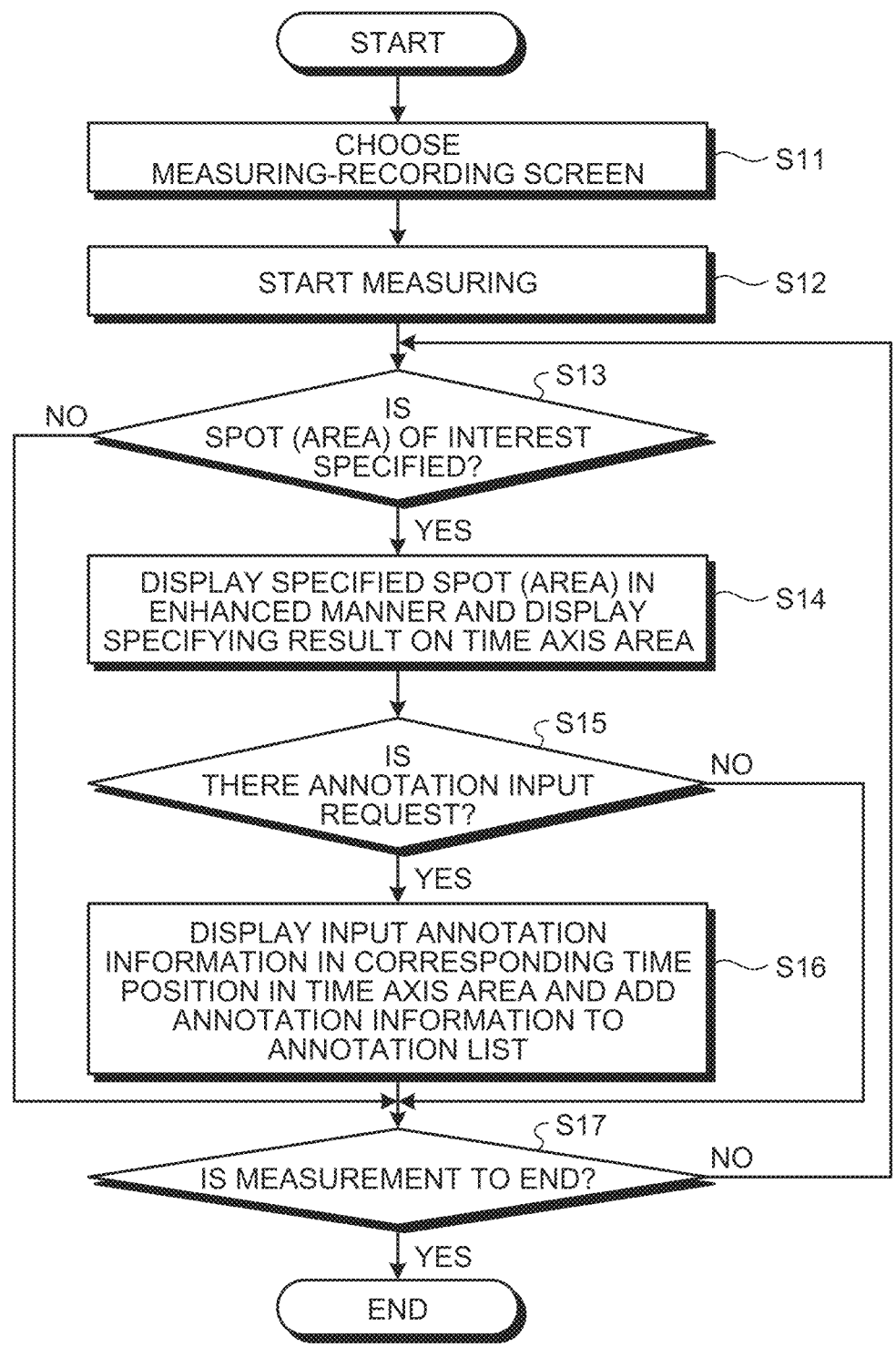
FIG. 8 is a flowchart of an information display process during measuring and recording.

FIG. 8 is a flowchart of the information display process at the stage of measuring and recording that is performed by the information display system 20. When "measuring-recording" is chosen on the start screen 204 illustrated in FIG. 2 (S11), measuring is started and waveforms of a plurality of signals are displayed along the same time axis in synchronization with one another (S12). The "signal waveforms" herein include both signal waveforms that are sensed by the sensors of the same type and signal waveforms that are detected by the sensors of different types.

The information display system 20 determines whether a spot or area of interest is specified on the displayed signal waveforms (S13). When a spot or area of interest is specified (YES at S13), the information display system 20 displays the specified spot in an enhanced manner in a signal waveform display area (the display parts 101 to 103) and displays the result of the specifying on a corresponding time position in a time axis area (the display part 110) (S14). The specifying result contains information representing that the specifying is performed or information identifying the specifying. Along with or before or after the display of the specifying result in the time axis area, the information display system 20 determines whether there is an annotation input request (S15). When there is an annotation input request (YES at S15), the information display system 20 displays the input annotation information in the corresponding time position in the time axis area and adds the annotation information to the annotation list (S16). The information display system 20 then determines whether a measurement end command is input (S17). When no position (area) of interest is specified (NO at S13) and when there is no annotation input request (NO at S15), the information display system 20 skips to step S17 to determine whether to end the measurement. The information display system 20 repeats steps S13 to S16 until the measurement ends (YES at S17).

The information display method provides the measuring-recording screen with high visibility of signal information when signals from a plurality of sensors are collected.

A method performed by the measurer to manually assign annotations has been described. The present invention enables, in addition to manual assignment by the measurer, automatic assignment of annotation using the following method.

The information display system 20 analyzes signals from the head position measurement device 50 and detects a shift in position of the head. For example, an optical tracking device is used as the head position measurement device 50. In the easiest method, when a measured position varies by a desired threshold or more, the information display system 20 determines that a shift in position occurs.

Figure 9:
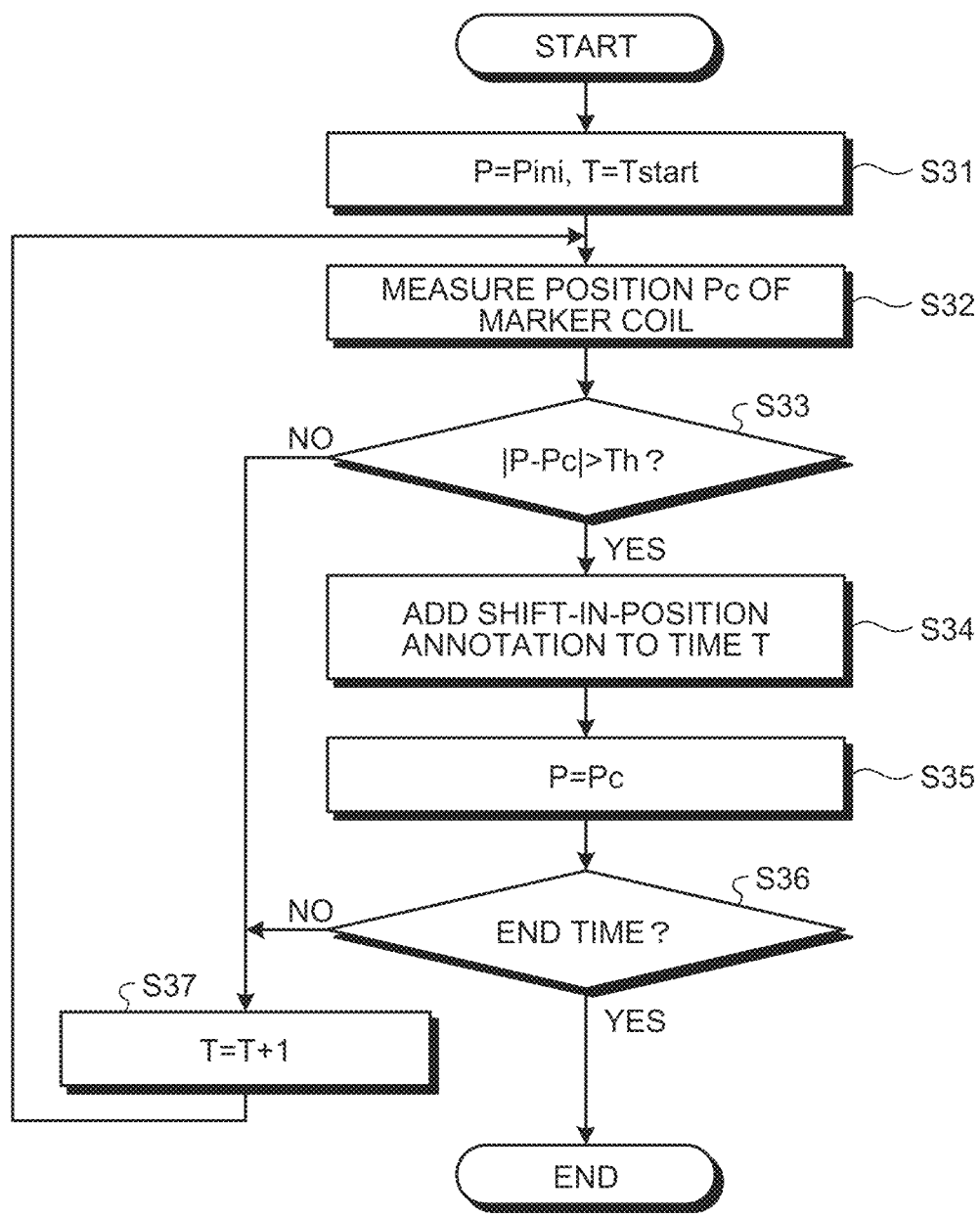
FIG. 9 is a flowchart of a flow of a process of determination on detection of a shift in position of a measurement part.

FIG. 9 is a flowchart of a flow of a process of determination on detection of a shift in position of a measurement part. As illustrated in FIG. 9, when starting shift-in-position determination, the information display system 20 sets an initial position Pini for a position P and a start time Tstart for a time T (S31). The information display system 20 then acquires a measured position Pc that is measured by a marker coil (S32).

When the difference between the measurement position Pc and the position P is above a threshold Th (YES at S33), the information display system 20 adds an annotation to the time T (S34).

The information display system 20 replaces the position P with the value of the measured position Pc (S35) and, when the time is an end time (YES at S36), the determination ends.

On the other hand, when the time is not the end time (NO at S36), the information display system 20 increments the time T (T=T+1) (S37) and returns to step S32.

When the difference is at or under the threshold Th (NO at S33), the information display system 20 increments the time T (T=T+1) (S37) and returns to step S32.

When a shift in position is detected, the information display system 20 assigns an annotation to the time of detection as in the manual assignment performed by the measurer. The information display system 20 saves the detected displacement information as information associated with the annotation. In the embodiment, the displacement information inclusive of the coordinates (positional information) of the head after the shift in position is saved.

FIG. 3 illustrates exemplary display of annotations (a head move start annotation 110b-1, a head move end annotation 110b-2, and a head move annotation 110b-3).

The coordinates of the head are necessary to estimate a signal source in the following process, such as dipole estimation. In the dipole estimation, when the head coordinates are not correct, the dipole is estimated in an incorrect position and there is a concern about effects on diagnosis. Using the head coordinates after the shift in position enables estimation of the dipole in a correct position.

Instead of the above-described embodiment illustrated in FIG. 3, only the head move end annotation 110b-2 may be displayed.

A shift in position does not necessarily occur instantaneously. In the case of slow move, a shift in position is completed over a time width to some extent. In order to deal with such a case, an annotation may have information on not a single time but multiple times, such as, a shift-in-position start time (the head move start annotation 110b-1) and an end time (the head move annotation 110b-3). In the following descriptions, the annotation that is automatically assigned herein is referred to as "shift-in-position annotation".

Operation During Analysis

Figure 10:
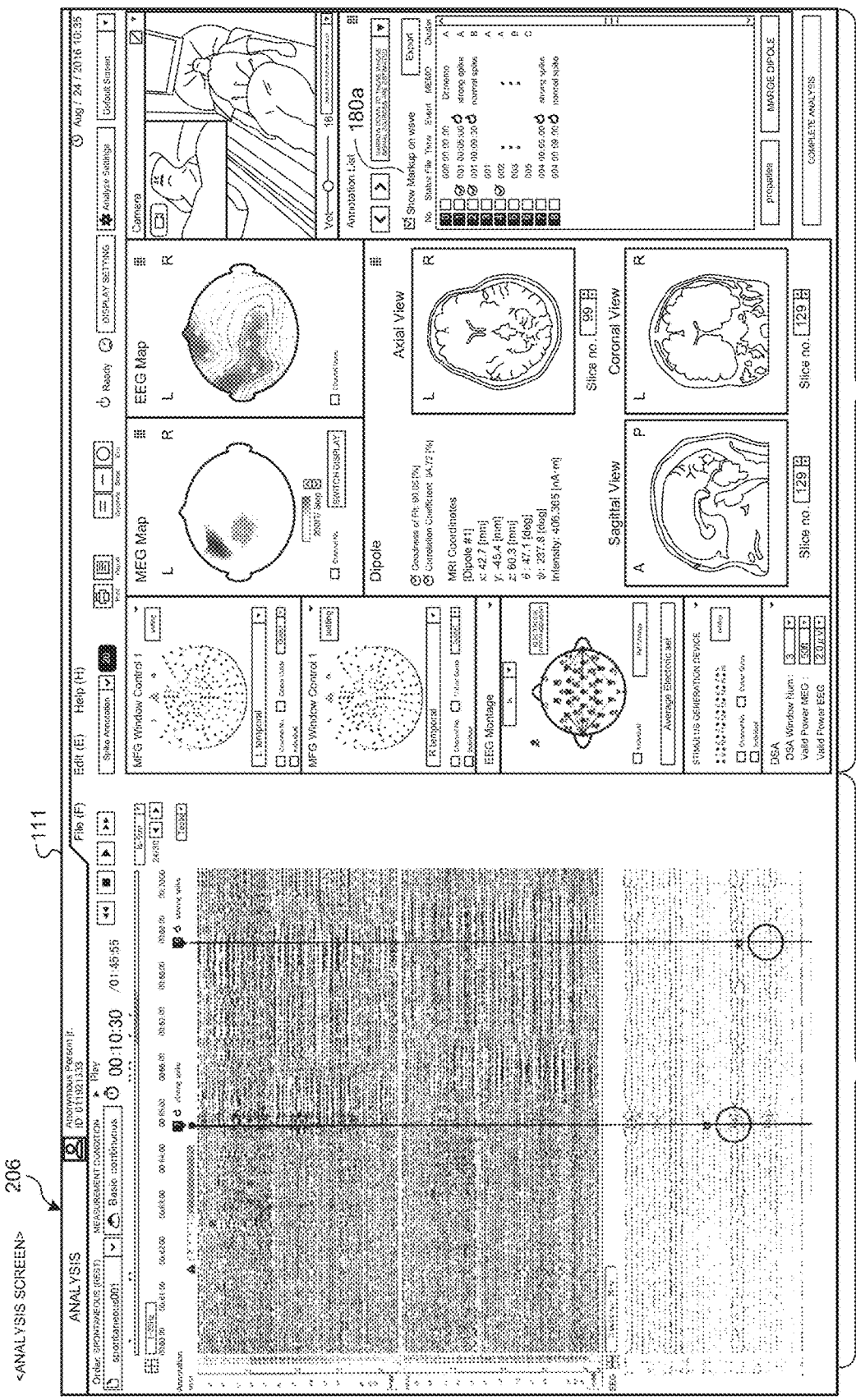
FIG. 10 is a diagram of an exemplary analysis screen.

FIG. 10 is a diagram illustrating an exemplary analysis screen 206 of the information display system 20 during analysis. The analysis screen is displayed by choosing the "analysis" button on the start screen 204 in FIG. 2. The tab 111 displays that this is an "analysis" screen. The analysis screen includes an area 202A to display recorded signal waveforms together with annotations and an area 202B to display analysis information. The area 202A to display the recorded signal waveforms and the annotation information is arranged on the left on the screen when viewed from the measurer and the area 202B to display the analysis information is arranged on the right when viewed from the measurer because this increases, during analysis, the efficiency of an operation to operate a mouse or the like to check or determine the analysis result in the area 202B while checking the signal waveforms or choosing a signal waveform in the area 202A.

In this example, the waveforms of the MEG signals in the second display parts 101 and 102 are displayed above the screen for the waveforms of the EEG signals in the second display part 103 of the area 202A. In the area 202B on the right of the area 202A, the MEG distribution maps 141 and 142 are displayed in a screen area on a side close to the area 202A and on the upper side of the screen and the EEG distribution map 130 is displayed under the MEG distribution maps 141 and 142. Thus, the analyzer is able to shift the view in the following order: "the waveforms of EEG signals" in the second display part 103, "the waveforms of MEG signals" in the second display parts 101 and 102, the MEG distribution maps 141 and 142, and the EEG distribution map 130 (in this case, clockwise). This enables efficient shift of the analyzer's (or observer's) view and accordingly enables improvement of the analysis operation efficiency. The clockwise shift has been described above; however, the shift is not limited to this example.

FIG. 10 illustrates that the whole analysis screen is displayed on the display screen of the single monitor display 26. Alternatively, the area 202A on the left and the area 202B on the right may be displayed independently on two or more monitor displays separately.

Figure 11:
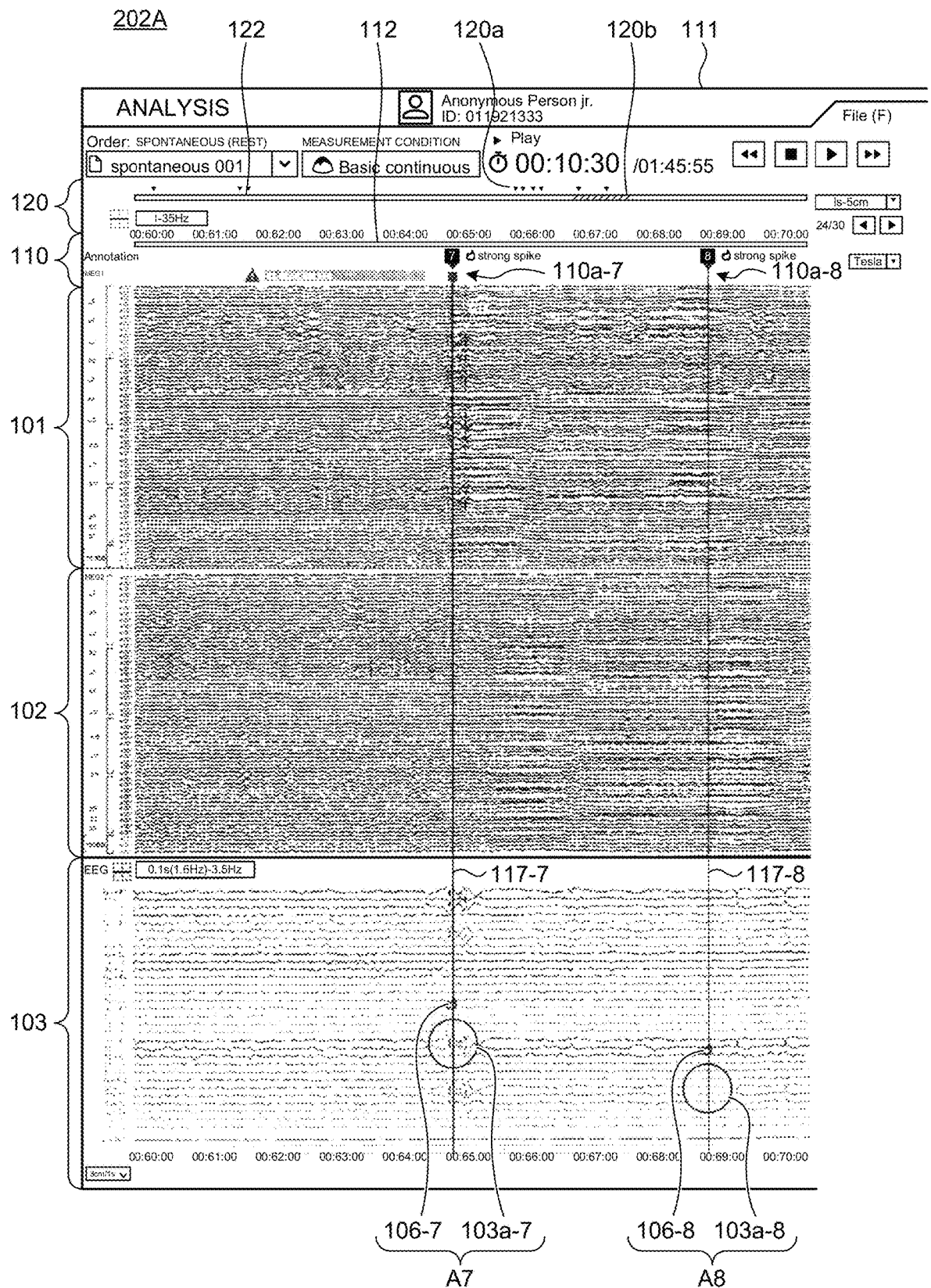
FIG. 11 is an enlarged view of the area on the left in the analysis screen.

FIG. 11 is an enlarged view of the area 202A on the left in the analysis screen in FIG. 10. The area 202A includes the display part 110 and a display part 120 to display time information during measuring in the horizontal direction of the screen (in the first direction) and the display parts 101 to 103 to display recorded signal waveforms in parallel in the vertical direction of the screen (in the second direction) according to each type.

In the display part 110, the time axis 112 representing the elapse of time during recording and annotations 110a-7 and 110a-8 that are added along the time axis 112 are displayed. In the display part 120, a time axis 122 representing the entire recording time is displayed. Along the time axis 122, pointer marks 120a each representing a time position to which an annotation is added and a time zone 120b representing the time band over which the signal waveforms currently displayed in the display parts 101 to 103 are recorded are displayed. The display enables the analyzer to intuitively grasp at which stage during measuring and recording the signal waveform currently being analyzed is acquired.

The analyzer is able to, after opening the analysis screen, for example, display signal waveforms in a requested time band by dragging the time zone 120b on the bar of the time axis 122. Alternatively, as describe below, by choosing a requested annotation from the annotation list 180, it is possible to display signal waveforms containing the signal waveform of the annotation and waveforms before and after the signal waveform on the display parts 101 to 103.

Annotations A7 and A8 that are added to the signal waveforms during recording are displayed in the display parts 101 to 103. Marks 103a-7 and 103a-8 are displayed in a highlighted manner and their corresponding attribute icons 106-7 and 106-8 are displayed near the marks 103a-7 and 103a-8. Furthermore, vertical lines 117-7 and 117-8 representing the time positions of the marks 103a-7 and 103a-8 are displayed. Displaying the line 117, for example, makes it possible to, when an annotation is added in connection with specifying a certain spot in the display part 103, easily check the result of the specifying by sight also in the display parts 102 and 101 that are signal display areas of a different type. The line 117 may be contained in the annotation information because the line 117 makes it easy to check the annotation information by sight and thus may be referred to as an "annotation line". Choosing the line 117 enables enlarged display of the signal waveforms in a certain period containing periods before after the time of the line 117. This process will be described below.

Figure 12:
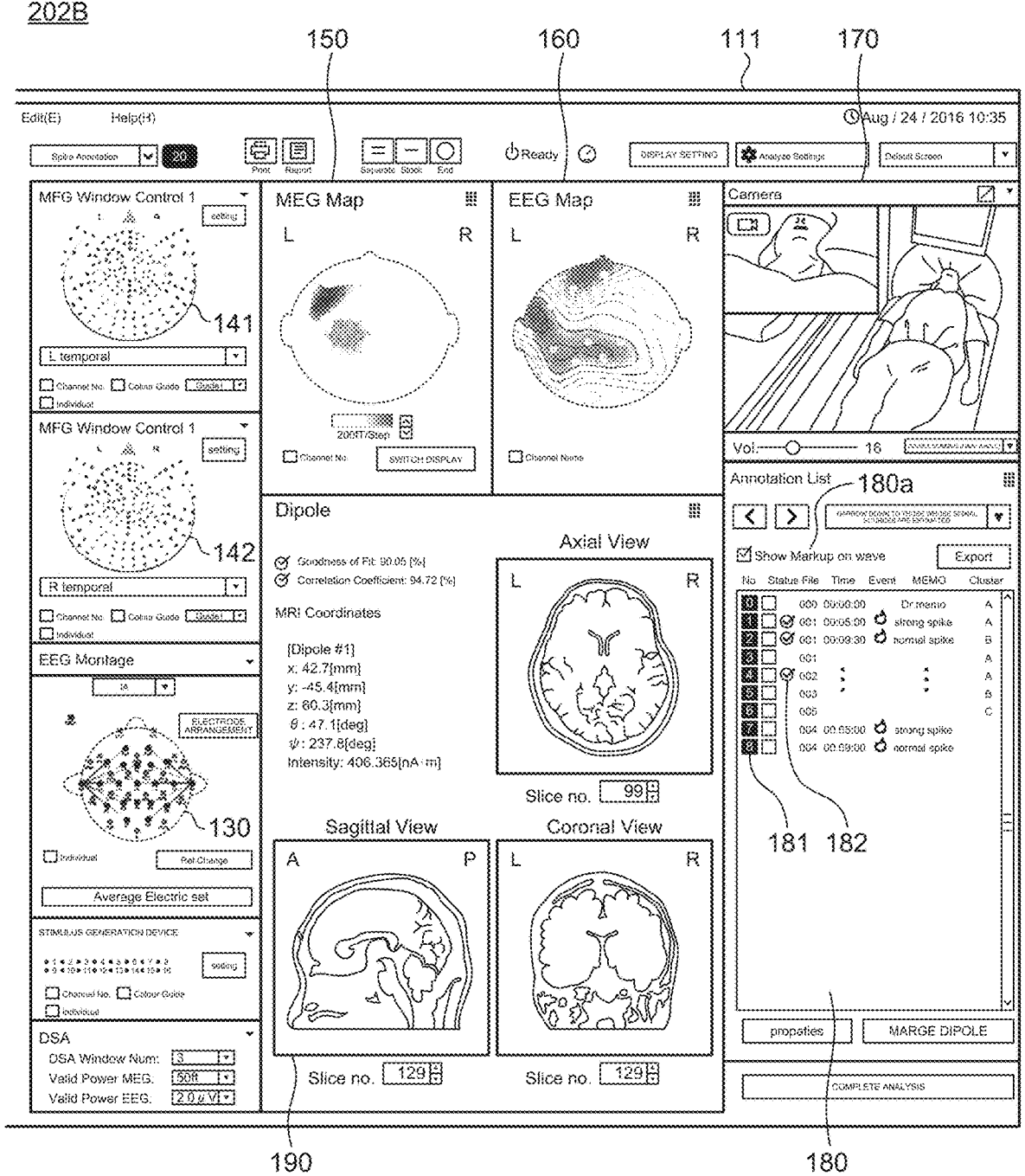
FIG. 12 is an enlarged view of the area on the right in the analysis screen.

FIG. 12 is an enlarged view of the area 202B on the right on the analysis screen at the same time as that in FIG. 11. The MEG distribution maps 141 and 142 corresponding to the signal waveforms that are displayed in the display parts 101 and 102 and the EEG distribution map 130 corresponding to the signal waveforms displayed in the display part 103 are displayed. Furthermore, an MEG (magnetoencephalograph) isofield contour map 150, an EEG (electroencephalograph) map area 160, and a display window 190 of tomographic images of the brain of the measurement subject that are acquired by MRI (Magnetic Resonance Imaging) are displayed. In the isofield contour map 150, the source area and the sink area are displayed in different colors and the direction of current flow is grasped by sight. The isofield contour map 150 and the map area 160 are information obtained after completion of the measurement and the MRI tomographic images are information obtained in a separate examination.

On the monitor window 170, a video of the measurement subject during measuring is displayed in synchronization with the time at which the signal waveforms in the display parts 101 to 103 are acquired. The analyzer is able to analyze the signal waveforms while watching the monitor window 170 to check the condition of the measurement subject.

In the annotation list 180, all annotations that are added during the measuring and recording are listed. Annotation information (such as an attribute icon and text input information) that is added in association with an annotation number 181 is on the annotation list 180. The annotation list 180 on the analysis screen is displayed, for example, in the ascending order (such that old data is on the top); however, the display is not limited thereto. As in the measuring-recording screen, using annotation numbers is not essential and an annotation may be identified according to a combination of, for example, a time, a file name and an attribute. The order in which the annotations contained in the annotation list 180 are displayed may be changed and may be sorted according to each item. Clicking the annotation number 181 or a row that is requested makes it possible to display, on the display parts 101 to 103 in FIG. 11, the signal waveforms over a certain time band containing the time positon to which the annotation is added.

Not as in the measuring-recording screen, estimation completion marks 182 (represented in FIG. 12) are displayed for annotations for which the analyzer has checked the signal waveforms of the annotation part and has estimated the signal source eventually.

When not-displaying is specified on the choice box 180a to choose displaying or not displaying the annotations, the attribute icons 106-7 and 160-8 in the display part 103 in FIG. 11 disappear. Not displaying the highlighted marks 103a-7 and 103a-8 may be chosen on the displaying/not-displaying choice box 180a.

Figure 13:
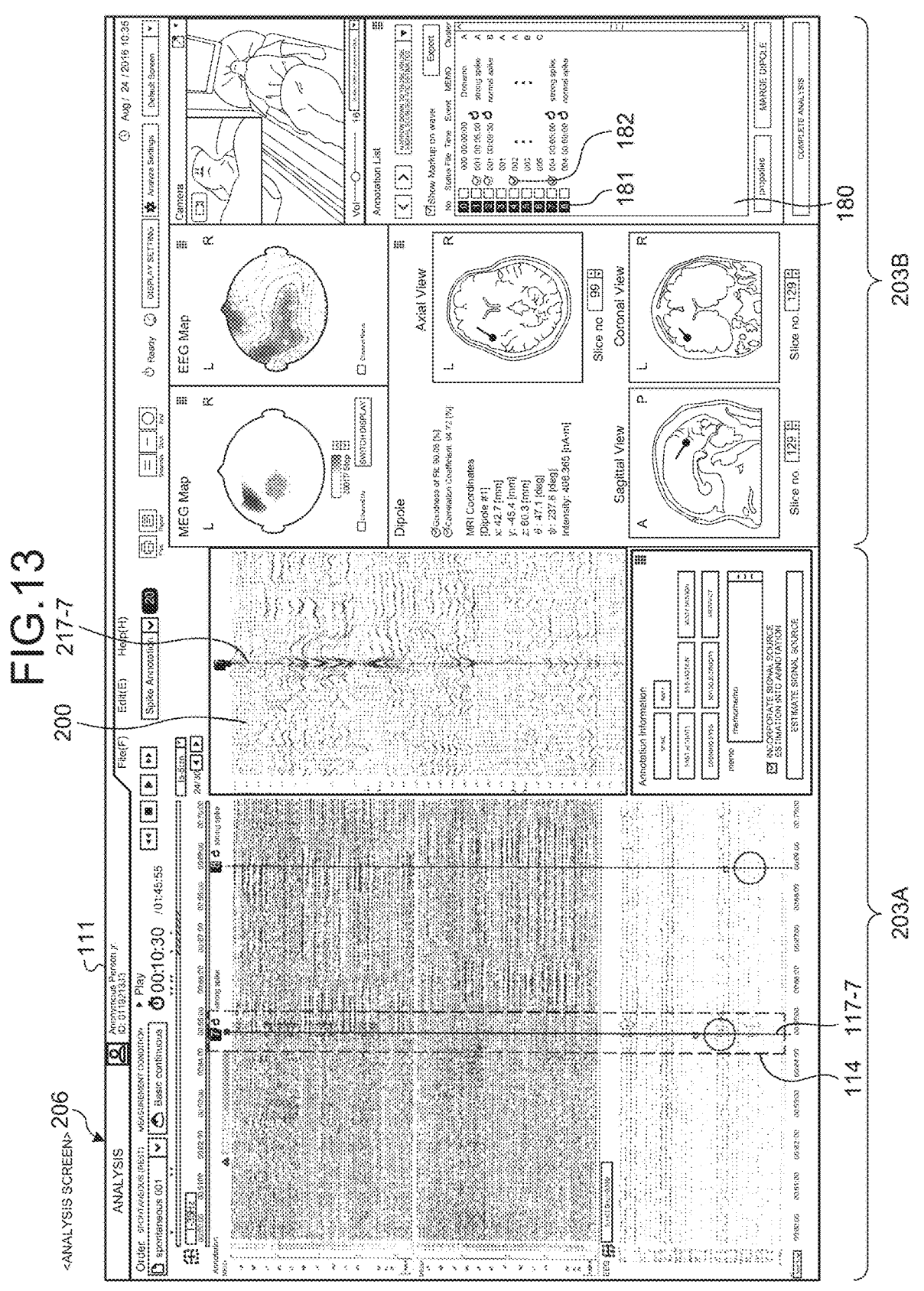

FIG. 13 is a diagram of a screen displayed right after a specific annotation line is chosen on the analysis screen in FIG. 11. FIG. 13 is a diagram of the whole screen displayed right after the line 117-7 is chosen on the analysis screen in FIG. 11. When the analyzer focuses on the annotation A7 and chooses (for example, double clicks) the line 117-7 in order to analyze the waveforms of the area, the signal waveforms near the highlighted signal waveforms are displayed in an enlarged manner in an enlarged display part 200. The signal waveforms are displayed in an enlarged manner in a certain time range represented by an area 114 together with a line 217-7 representing a time position.

Figure 14:
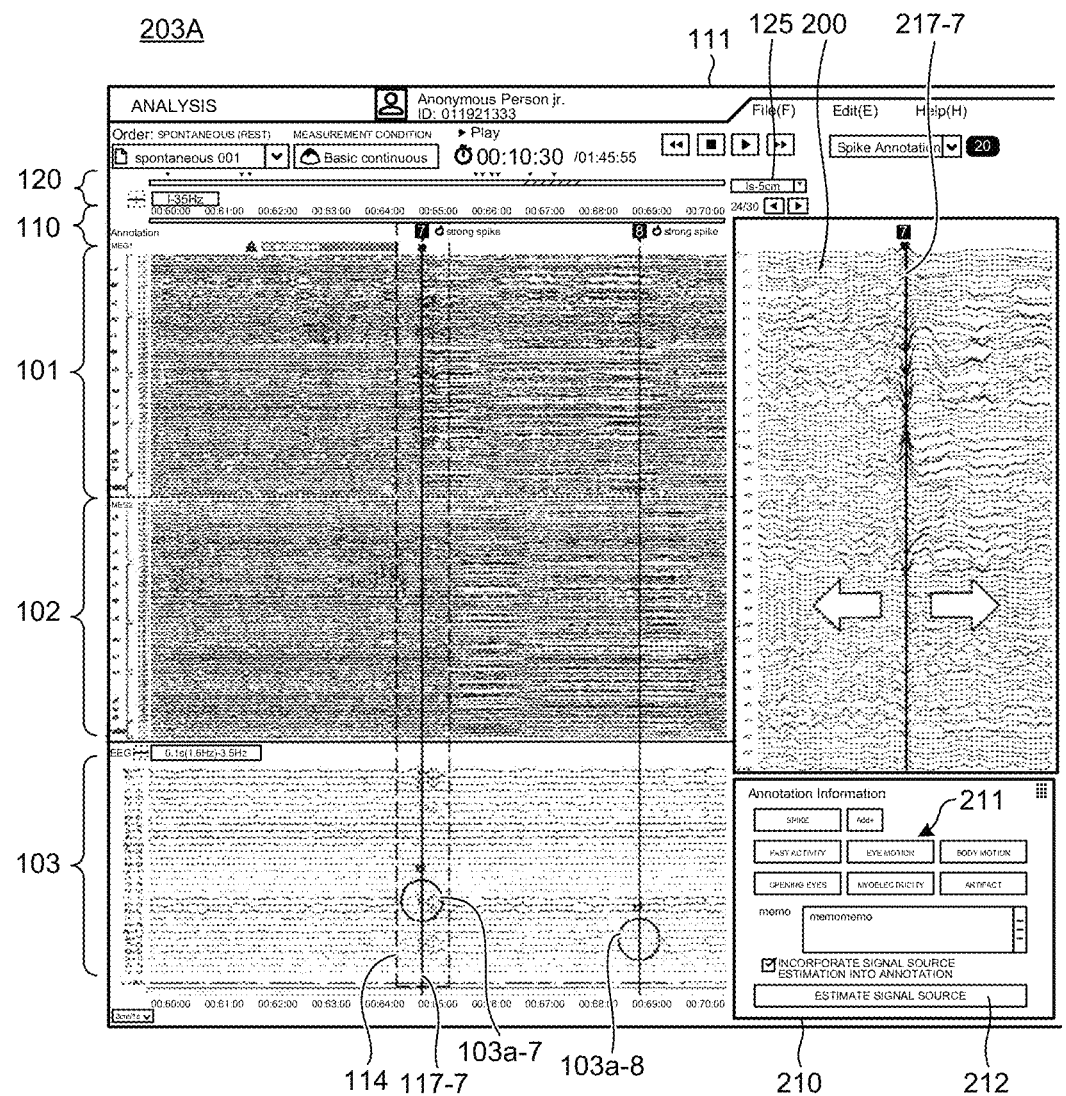
FIG. 14 is an enlarged view of the area on the left in FIG. 13.

FIG. 14 is an enlarged view of an area 203A (a signal waveform display area) on the left in FIG. 13. Displaying the signal waveforms in an enlarged manner in the enlarged display part 200 enables the analyzer to re-check adequacy of the mark added during recording or check the waveform parts that are not checked during measuring and recording. For example, it is possible to accurately specify or change a correct spot of a problematic waveform by dragging the line 217-7 horizontally. Any one or both of the mark 103a displayed in a highlighted manner and the attribute icon 106 in the display part 103 may be incorporated into the enlarged display part 200. Note that, this may hinder checking by sight to accurately determine an amplitude singularity and therefore it is desirable that it is possible to, when the highlighted mark 103a and the attribute icon 106 are displayed in the enlarged display part 200, choose to display or not to display the highlighted mark 103a or the attribute icon 106.

It is also possible to specify a type of signal waveforms displayed in the enlarged display part 200 and a channel range. For example, the analyzer shifts the view from the highlighted mark 103a-7 to an upper side of the screen and checks whether there is an amplitude singularity in the waveforms in the display parts 101 and 102 for MEG waveforms. In this case, by inputting a targeted channel area for the display part 101 or 102 in a box 125, it is possible to display the MEG waveforms relating to the mark 103a-7 in an enlarged manner in the enlarged display part 200.

A confirmation window 210 is displayed on a lower side of the screen of the enlarged display part 200. The confirmation window 210 contains signal waveform attribute buttons 211 and a signal source estimation button 212. The attribute button 211 corresponds to the attribute information contained in the pop-up window 115 on the measuring-recording screen and, when the attribute added during recording is incorrect, it is possible to choose the attribute button 211 to choose a correct attribute. When any one of or both of the correct signal waveform position and the choice of attribute are confirmed, clicking the estimation button 212 enables incorporation of the signal source estimation into the annotation.

Figure 15:
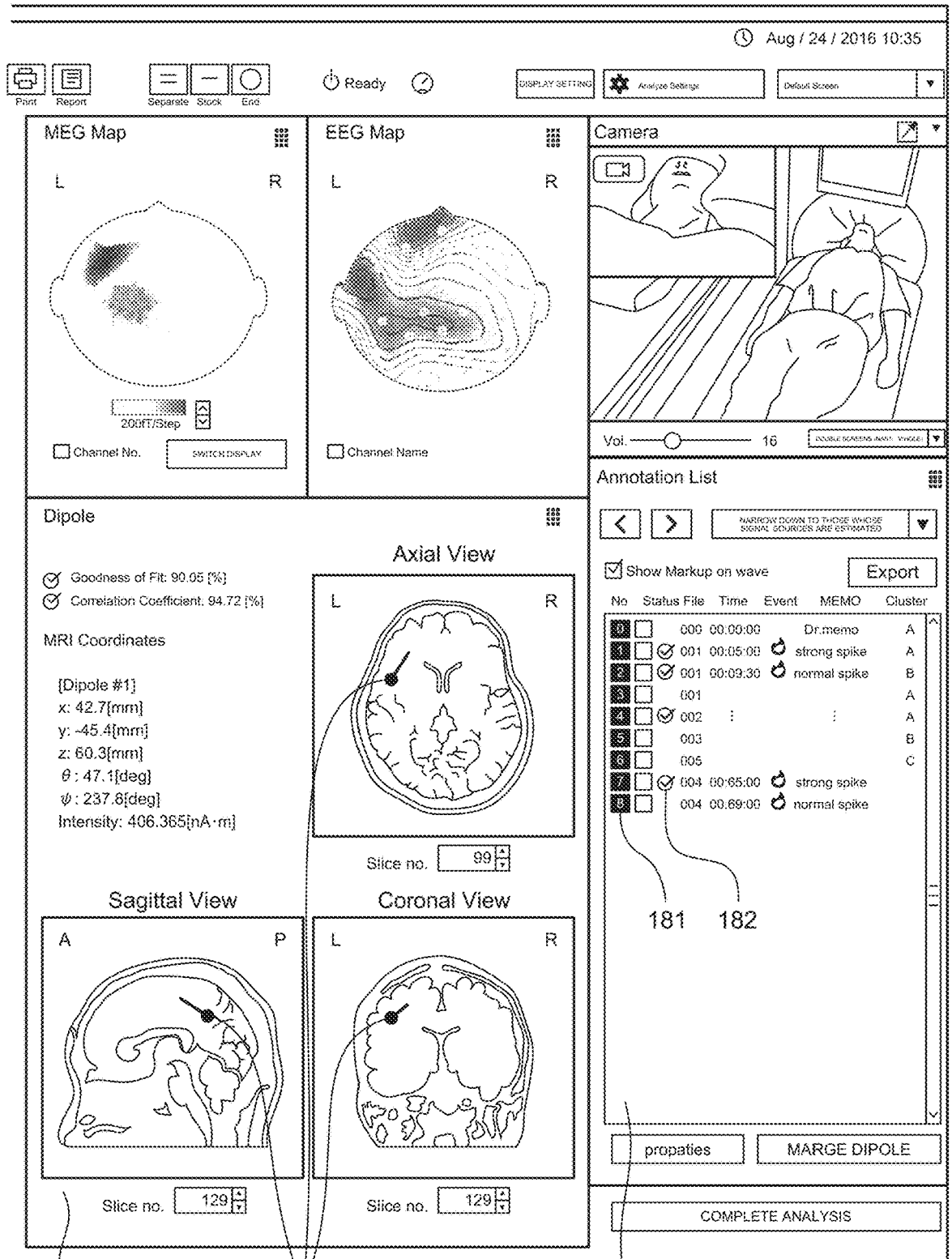
FIG. 15 is an enlarged view of the area on the right in FIG. 13.

FIG. 15 is an enlarged view of an area 203B on the right in FIG. 13. When any one or both of the signal waveform position and the attribute are confirmed with respect to the requested annotation and the signal source estimation button 212 is chosen, the estimation completion mark 182 is added to the corresponding annotation (in this example, the annotation number "7") on the annotation list 180. Furthermore, a dipole estimation result 190a is displayed on the MRI tomographic images on the display window 190.

As the position of the head that is used to estimate a dipole, the position that is saved with the latest shift-inposition annotation before the time that is currently focused on. When there is no shift-in-position annotation before the time that is currently focused on, the position of the head that is calculated at the start of measurement is used.

Accordingly, even when the head moves during measurement, it is possible to estimate a dipole in a correct position.

To perform current source estimation, such as dipole estimation, it is necessary to calculate a relationship between a source of current and a sensor. In the process, the position of the head is necessary and a time for the process is required. For this reason, in general, the calculation of this process is often performed in advance before analysis using a spare time during measurement.

In the embodiment, each time a shift in position occurs and the shift in position is detected, a shift-in-position annotation is automatically assigned. Thus, it can be regarded that no shift in position is detected between shift-in-position annotations and the position of the head is the same between the annotations. Accordingly, calculating in advance the relationship between the source of current and the sensor with respect to each area that is sectioned by shift-in-position annotations enables quick analysis.

There are two types of method of updating the annotation list 180 when any one or both of the mark positions, which are displayed in a highlighted manner in the display parts 101 to 103, and the content of the annotations 110a are changed by an analyzer. The methods include a method of incorporating only the latest information updated by the analyzer into the annotation list 180 and a method of maintaining the annotation information during measuring and recording and adding the annotation information as new annotation information. When the latter method is employed, for example, a branch number from the annotation number during recording may be added as annotation identification information. In this case, new annotation information may be added also to the display part 110 and the added annotation information may be displayed in a different color along the time axis.

Figure 16:
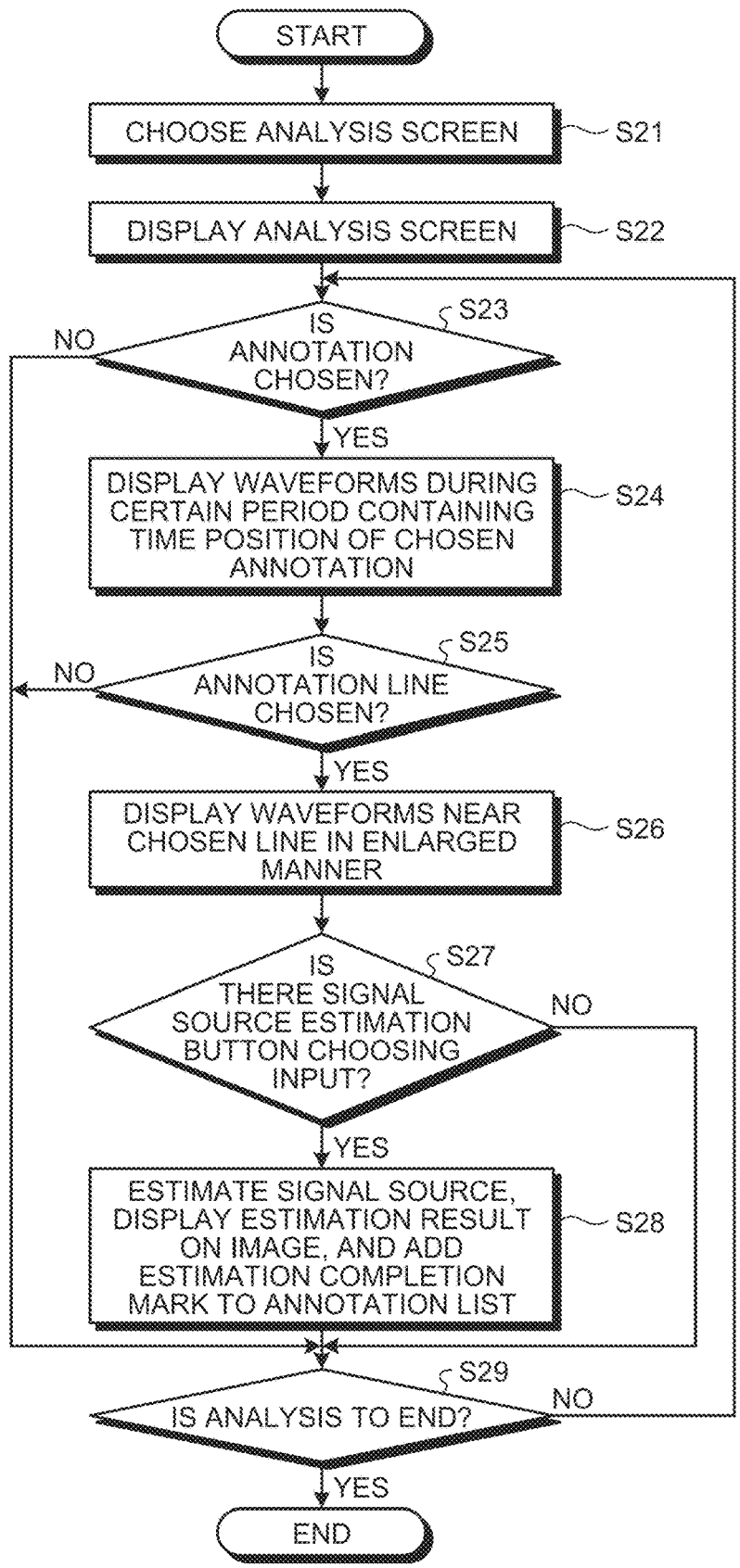
FIG. 16 is a flowchart of an information display process during analysis.

FIG. 16 is a flowchart of an information display process during analysis that is performed by the information display system 20. When "analysis" is chosen on the start screen 204 (see FIG. 2) (S21), analysis is started and the analysis screen is displayed (S22). The initial analysis screen may be a blank screen without any display of signal waveforms or there may be signal waveforms in a certain time range on the top or end of recording. When the analysis screen is displayed, whether a given annotation is chosen is determined (S23). An annotation may be chosen by choosing a given annotation number or a given row in the annotation list 180 or specifying a time position by operating the time zone 120b on the time axis 122 in the display part 120. When an annotation is chosen (Yes at S23), signal waveforms during a certain period containing the time position of the chosen annotation are displayed (S24).

Whether the line 117 representing the time positon of a mark displayed in a highlighted manner is chosen on the displayed screen is determined (S25). When the line 117 is chosen (YES at S25), the signal waveforms during the certain time range containing the chosen line 117 are displayed in an enlarged manner (S26). Enlarged display is not necessarily limited to signal waveforms near the mark that is displayed in a highlighted manner and a different type of signal waveform in the same time position may be displayed in an enlarged manner. For example, when a mark displayed in a highlighted manner is added to EEG signal waveforms, MEG signal waveforms in the same time position may be displayed in an enlarged manner. Furthermore, instead of displaying signal waveforms of all channels in an enlarged manner, signal waveforms acquired in a given range of channels containing the channel in which the marked signal waveforms are acquired may be displayed in an enlarged manner. In this case, any one of or both of a type of signal waveform to be displayed in an enlarged manner and whether there is an input to specify a cannel range may be determined.

Whether the signal source estimation button 212 is pressed is determined (S27). When the signal source estimation button 212 is pressed (YES at S27), computing to estimate a signal source is performed.

As the position of the head that is used to estimate a dipole, a position that is saved together with the latest shift-in-position annotation before a time that is currently focused on is used. When there is no shift-in-position annotation before the time that is currently focused on, the position of the head that is calculated at the start of measurement is used.

The result of estimation is displayed in MRI tomographic images and the estimation completion mark 182 is added to the annotation list 180 (S28). Then, whether an analysis end command is input is determined (S29). When no annotation is chosen (NO at S23), no annotation line is clicked for enlarged display (NO at S25) and no input is made to choose the signal source estimation button (NO S27), skip to step S29 and whether to end the analysis is determined. Until an analysis end command is input (YES at S29) steps S23 to S28 are repeated.

Whether the annotation is changed may be determined between steps S26 and S27. When the annotation is changed, the change is incorporated into the annotation list 180 and the process moves to the determination at step S27.

The above-described display processing operations enables information display with excellent visibility and operability.

Figure 17:
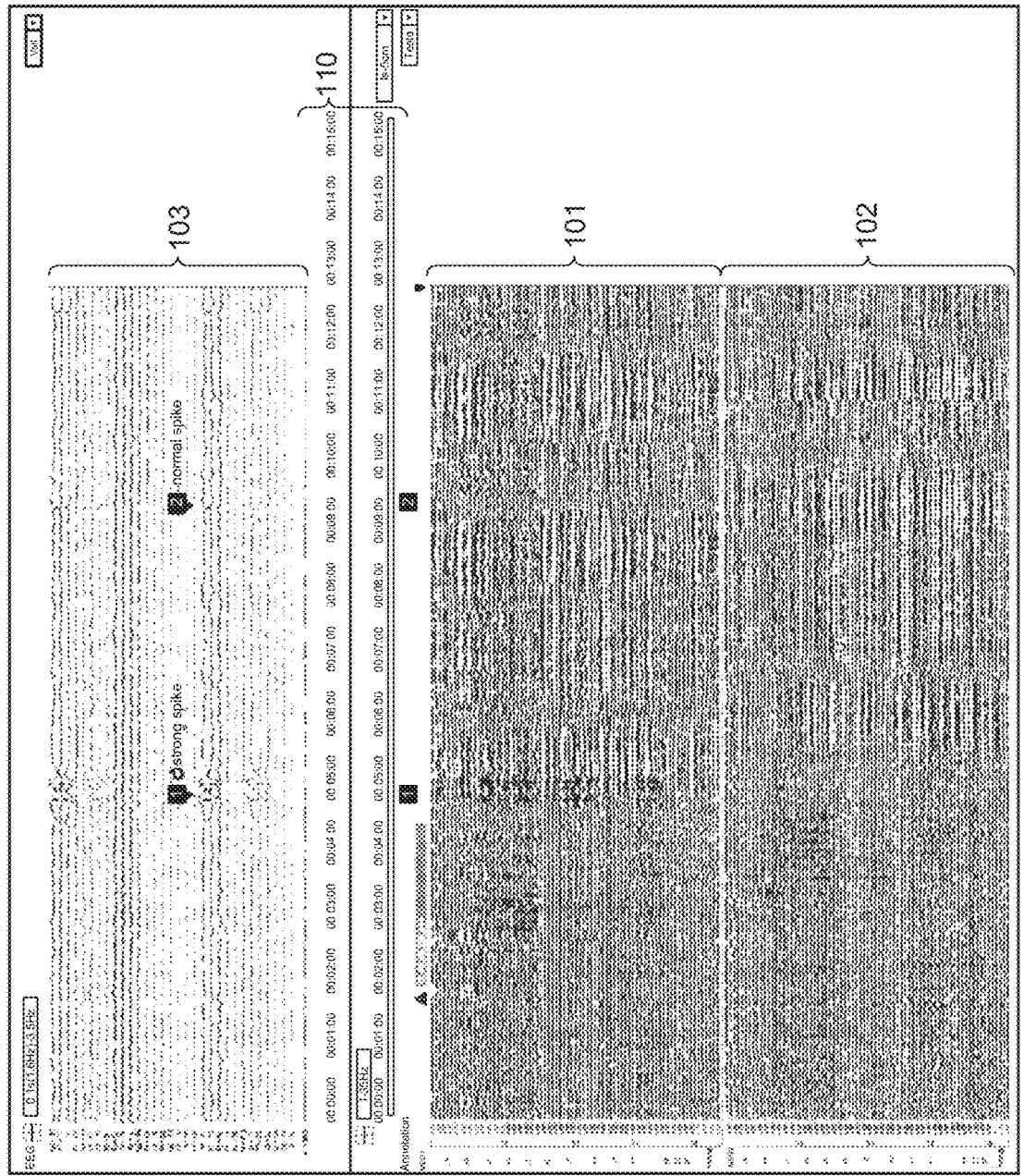
FIG. 17 is a diagram of a modification of a display layout.
Figure 18:
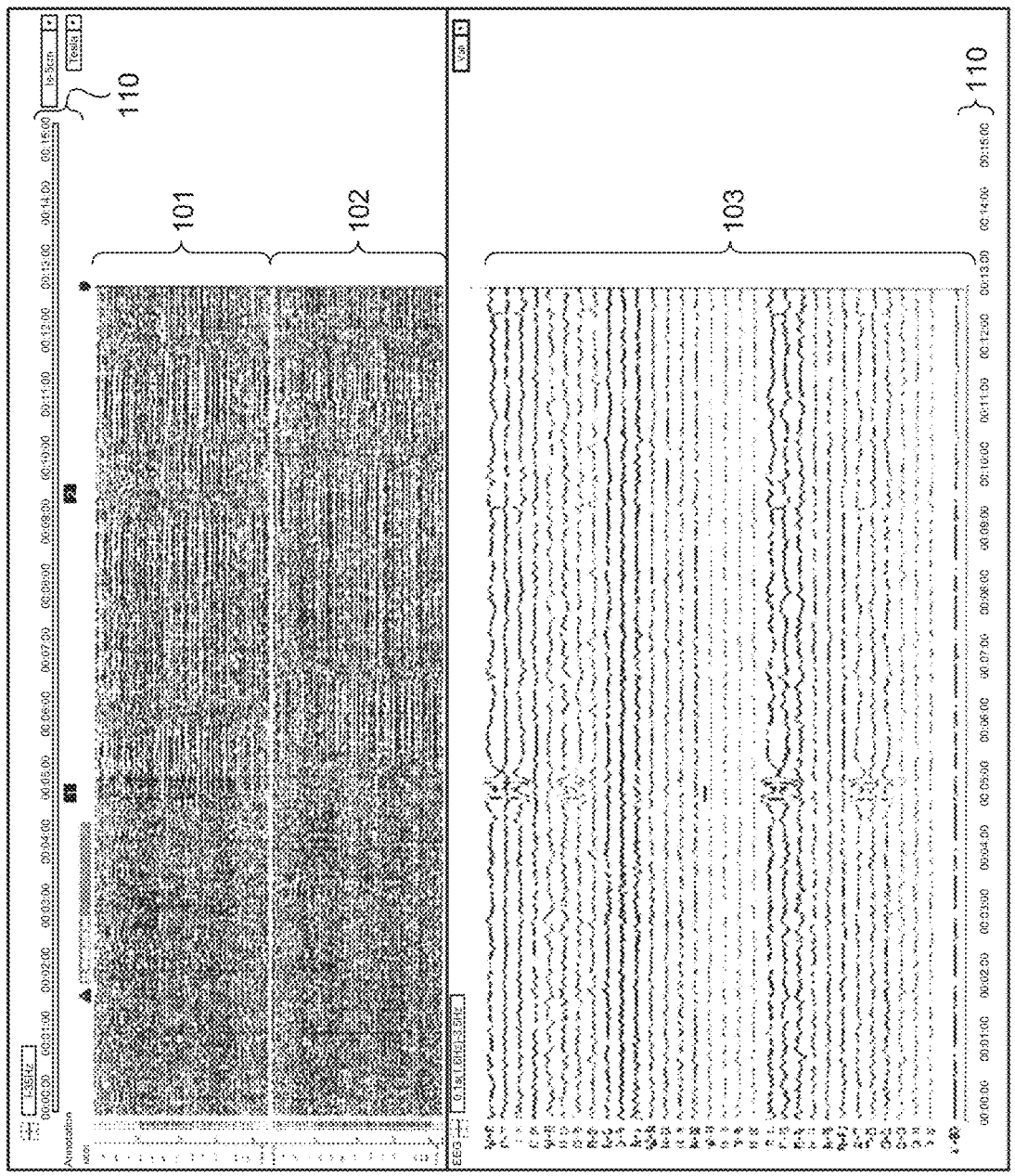
FIG. 18 is a diagram of another modification of the display layout.

FIG. 17 and FIG. 18 are diagrams illustrating a modification of the display layout. When displaying signal waveforms from multiple types of sensor, it is possible to set a display position properly according to the signal type. For example, as illustrated in FIG. 17, the display part 103 to display EEG signal waveforms whose amplitude is large and easy to view may be arranged in on an upper side of the screen. In this case, the MEG distribution maps 141 and 142 are arranged on the right of the display parts 101 and 102 and the EEG distribution map 130 is arranged on the right of the display part 103 and above the MEG distribution maps 141 and 142. Furthermore, as illustrated in FIG. 18, the vertical size of a given display part may be changed. For example, by choosing the frame of the display part 103 to display EEG waveforms and moving the frame in the vertical direction of the screen, it is possible to change the ratio between the vertical sizes of the display part 103 and the display parts 101 and 102.

The position of the display part 110 to display the timeline is not limited to the upper end and lower end of the screen. The display unit 110 may be provided between the MEG waveforms and the EEG waveforms. For example, a timeline extending horizontally between the MEG waveforms and the EEG waveforms and a timeline arranged on any one of or both of the upper end and the lower end of the screen may be combined.

Figure 19:
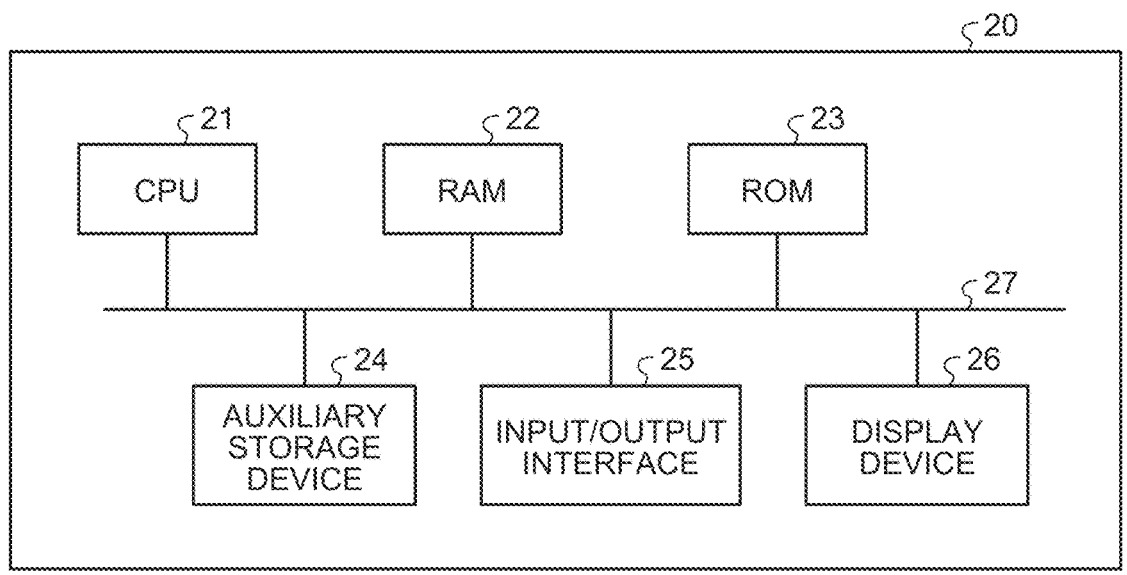
FIG. 19 is a hardware configuration diagram of an information display system.

FIG. 19 is a hardware configuration diagram of the information display system 20. The information display system 20 includes a central processing unit (CPU) 21, a random access memory (RAM) 22, a read only memory (RAM) 23, an auxiliary storage device 24, an input/output interface 25, and the display device 26 that are connected to one another via a bus 27.

The CPU 21 controls entire operations of the information display system 20 and performs various types of information processing. The CPU 21 also executes an information display program that is stored in the ROM 23 or the auxiliary storage device 24 to control operations to display the measuring-recording screen and the analysis screen. The RAM 22 is used as a work area of the CPU 21, and the RAM 22 may include a non-volatile RAM that stores main control parameters and information. The ROM 23 stores a basic input/output program, etc. The information display program according to the invention may be saved in the ROM 23. The auxiliary storage device 24 is a storage device, such as a solid state drive (SSD) or a hard disk drive (HDD) and stores, for example, a control program to control operations of the information display system 20 and various types of data and files necessary for operations of the information display system 20. The input/output interface 25 includes both a user interface, such as a touch panel, a keyboard, a display screen, or an operation button, and a communication interface that loads information from various sensors or the data recording server 42 and outputs analysis information to another electronic device. The display device 26 corresponds to the monitor display 26 in FIG. 1. The display device 26 displays the measuring-recording screen and the analysis screen and updates the screen according to the input and output operations via the input/output interface 25.

Figure 20:
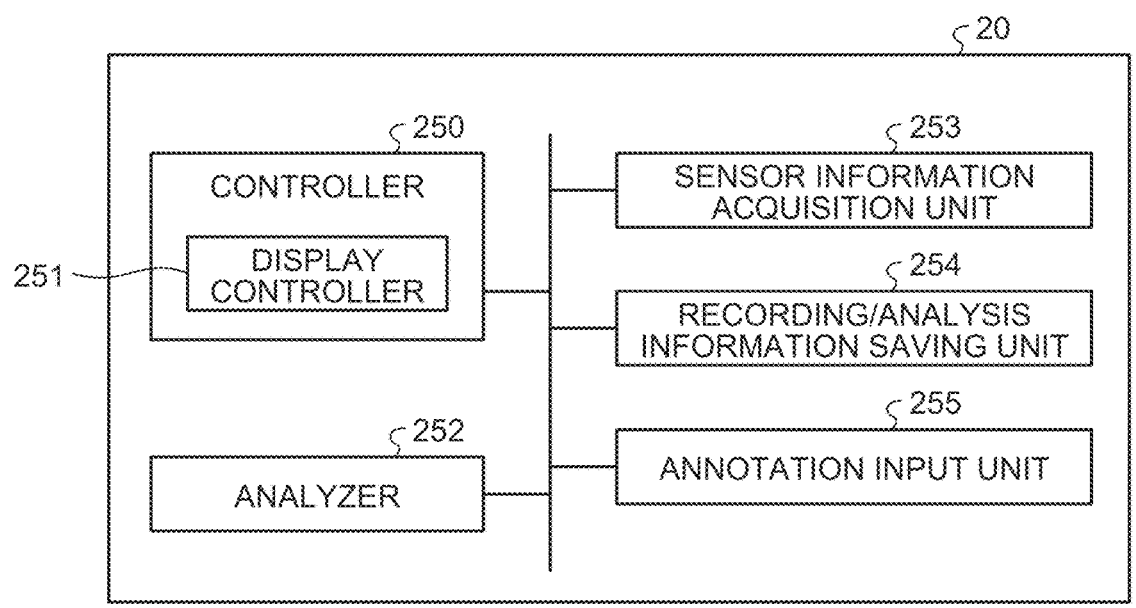
FIG. 20 is a functional block diagram of the information display system.

FIG. 20 is a functional block diagram of the information display system 20. The information display system 20 includes a controller 250, an analyzer 252, a sensor information acquisition unit 253, a recording/analysis information saving unit 254 and an annotation input unit 255. The controller 250 includes a display controller 251 that controls the screen display of the information display system 20.

The sensor information acquisition unit 253 acquires sensor information from the measurement device 3 or the data recording server 42. The annotation input unit 255 inputs annotation information to be added to the sensor information. The analyzer 252 analyzes the collected sensor information. Analyzing the sensor information includes analyzing signal waveforms, analyzing an amplitude singularity, and analyzing brain magnetic fields containing the orientation of a current dipole. In this example, the analyzer 252 has a function of estimating a signal source corresponding to an annotation that is chosen from the analysis screen (function of an estimator). The display controller 251 controls the screen displays of sensor information during measuring and recording and analysis according to the method described with reference to FIGS. 2 to 18. The recording/analysis information saving unit 254 saves the measurement data and the analysis result. When an annotation is added to the signal waveforms during measuring and recording, the annotation is saved in association with information about the time at which the signal waveforms are acquired. The functions of the controller 250 including the display controller 251 are implemented by the CPU 21 in FIG. 19 by loading the program that is stored in the ROM 23, or the like, into the RAM 22 and executing the program. The function of the analyzer 252 is also implemented by the CPU 21 by loading the program that is stored in the ROM 23, or the like, into the RAM 22 and executing the program. Alternatively, for example, at least part of the functions of the controller 250 and the analyzer 252 may be realized by a dedicated hardware circuit (semiconductor integrated circuit). The functions of the sensor information acquisition unit 253 and the annotation input unit 255 are implemented by the input/output interface 25. The function of the recording/analysis information saving unit 254 is implemented by the ROM 203 or the auxiliary storage device 24.

When operations of the information display system of the embodiment are implemented by executing the information display program, the information display program causes the CPU 21 to execute (a) a procedure to display a signal detection time axis in a first direction of a displayed first display part screen, (b) a procedure to display a plurality of waveforms that are acquired by measuring signals on a displayed second display part in parallel in a second direction different from the first direction, and (c) a procedure to, when a spot on at least a waveform of the signal waveforms or an area near the waveform is specified on the second display part, display the specified spot in an enhanced manner and display a result of the specifying as specifying information in a time position on the first display part corresponding to the specified spot.

Installing such an information display program in the information display system makes it possible to easily check by sight a position or a range (area) of interest on a screen on which a plurality of signal waveforms are displayed on the same time axis.

As described above, according to the embodiment, realizing a display screen on which move of a measurement part is specified easily and that is easy to view enables, even when the measurement part moves, prevention of incorrect analysis and analysis in a short time.

In the above-described embodiment, the measurement device 3 is configured to collect EEG signals and MEG signals; however, the measurement device 3 is not limited thereto. For example, the measurement device 3 may collect MEG signals, an electroencephalograph different from the measurement device 3 may collect EEG signals, and the respective sets of biological signals may be output from the measurement device 3 and the electroencephalograph to the data recording server 42.

The embodiments produce an effect that it is possible to realize a display screen on which displacement of a measurement part is specified easily and that is easy to view.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information display system comprising:
at least one biological signal measurement device configured to collect biological signals from a patient;
an optical tracking device configured to detect a current position of a measurement part of the patient and output a signal indicating the current position;
a display unit configured to display a time axis of signal detection; and
a controller configured to control the optical tracking device and the display unit,
the controller is further configured to determine that displacement of the measurement part is detected based on the output signal of the optical tracking device, the determining that displacement of the measurement part is detected including measuring a distance of displacement of the current position of the measurement part of the patient from an original position of the measurement part, and determining whether the distance of displacement meets a desired threshold distance, and
display the collected biological signals on the time axis of the display unit in synchronization with detection information representing that the displacement is detected in any one of a time position and a time area on the display unit in which the displacement is detected, and display displacement information in association with the detection information and the collected biological signals in the any one of the time position and the time area in which the displacement is detected.

2. The information display system according to claim 1, wherein
the controller is further configured to store in memory of the information display system the displacement information in association with the detection information.

3. The information display system according to claim 2, wherein
the controller is further configured to store in the memory, as the displacement information, positional information on the measurement part after the displacement.

4. The information display system according to claim 2, wherein
the controller is further configured to store in the memory a time of start of displacement of the measurement part and a time of end of the displacement as the displacement information.

5. An information display device comprising:
a display unit configured to display a time axis of signal detection; and
a controller configured to,
control at least one biological signal measurement device configured to collect biological signals from a patient,
control an optical tracking device configured to detect a current position of a measurement part of the patient and output a signal indicating the current position,
measure a distance of displacement of the current position of the measurement part of the patient from an original position of the measurement part based on the output signal of the optical tracking device,
determine that displacement of the measurement part is detected based on the output signal of the optical tracking device, the determining that displacement of the measurement part is detected using the measured distance of displacement, and determining whether the distance of displacement meets a desired threshold distance, and
display the collected biological signals on the time axis of the display unit in synchronization with detection information representing that the displacement is detected in any one of a time position and a time area on the display unit in which the displacement is detected, and display displacement information in association with the detection information and the collected biological signals in the any one of the time position and the time area in which the displacement is detected.

6. The information display device according to claim 5, wherein
the controller is further configured to save in memory the displacement information in association with the detection information.

7. The information display device according to claim 6, wherein
the controller is further configured to store in memory, as the displacement information, positional information on the measurement part after the displacement.

8. The information display device according to claim 6, wherein
the controller is further configured to store in memory a time of start of displacement of the measurement part and a time of end of the displacement as the displacement information.

9. A non-transitory computer-readable recording medium including computer readable instructions, which when executed by a computer, causes the computer to:
display a time axis of signal detection on a display unit;
control at least one biological signal measurement device such that the at least one biological signal measurement device collects biological signals from a patient; and
control an optical tracking device such that the optical tracking device detects a current position of a measurement part of the patient and outputs a signal indicating the current position;
determine that displacement of the measurement part is detected based on the output signal of the optical tracking device, the determining that displacement of the measurement part is detected including measuring a distance of displacement of the current position of the measurement part of the patient from an original position of the measurement part, and determining whether the distance of displacement meets a desired threshold distance; and display the collected biological signals on the time axis of the display unit in synchronization with detection information representing that the displacement is detected in any one of a time position and a time area on the display unit in which the displacement is detected, and display displacement information in association with the detection information and the collected biological signals in the any one of the time position and the time area in which the displacement is detected.

10. The information display system according to claim 1, wherein the at least one biological signal measurement device is a plurality of biological signal measurement devices configured to collect a plurality of biological signals from the patient, and wherein the controller is further configured to display the collected plurality of biological signals on the time axis of the display unit in synchronization with the detection information.

11. The information display system according to claim 10, wherein the plurality of biological signal measurement devices includes at least one of:

an electroencephalograph (EEG) device, a magnetoencephalograph (MEG) device, a magnetic resonance imaging (MRI) device, a heart rate monitoring device, an intrauterine pressure monitoring device, or any combinations thereof.

12. The information display system according to claim 10, wherein the controller is further configured to display annotations input by a medical professional on time axis of the display unit in synchronization with the collected biological signals and the detection information.

13. The information display system according to claim 10 wherein:

the optical tracking device includes a camera configured to record live video of the patient, and wherein the controller is further configured to display the live video of the patient in synchronization with the collected biological signals and the detection information.

14. The information display device according to claim 5, wherein the at least one biological signal measurement device is a plurality of biological signal measurement devices; and the controller is further configured to, receive a plurality of biological signals collected from the patient from the plurality of biological signal measurement devices, and display the collected plurality of biological signals on the time axis of the display unit in synchronization with the detection information.

15. The information display device according to claim 14, wherein the plurality of biological signal measurement devices includes at least one of:

an electroencephalograph (EEG) device, a magnetoencephalograph (MEG) device, a magnetic resonance imaging (MRI) device, a heart rate monitoring device, an intrauterine pressure monitoring device, or any combinations thereof.

16. The information display device according to claim 14, wherein the controller is further configured to display annotations input by a medical professional on time axis of the display unit in synchronization with the collected biological signals and the detection information.

17. The information display device according to claim 14, wherein the controller is further configured to:

receive live video of the patient from the optical tracking device; and display the live video of the patient in synchronization with the collected biological signals and the detection information.

18. The non-transitory computer-readable recording medium according to claim 9, wherein the at least one biological signal measurement device is a plurality of biological signal measurement devices; and the computer is further caused to, receive a plurality of biological signals collected from the patient from the plurality of biological signal measurement devices, and display the collected plurality of biological signals on the time axis of the display unit in synchronization with the detection information.

19. The non-transitory computer-readable recording medium according to claim 18, wherein the plurality of biological signal measurement devices includes at least one of:

an electroencephalograph (EEG) device, a magnetoencephalograph (MEG) device, a magnetic resonance imaging (MRI) device, a heart rate monitoring device, an intrauterine pressure monitoring device, or any combinations thereof.

20. The non-transitory computer-readable recording medium according to claim 18, wherein the computer is further caused to:

display annotations input by a medical professional on time axis of the display unit in synchronization with the collected biological signals and the detection information.

* * * * *